US008658176B2

(12) United States Patent
Leng et al.

(10) Patent No.: US 8,658,176 B2
(45) Date of Patent: Feb. 25, 2014

(54) LIPIDATED TUMOR-ASSOCIATED ANTIGENS AND IMMUNOTHERAPEUTIC COMPOSITIONS

(75) Inventors: Chih-Hsiang Leng, Miaoli County (TW); Hsin-Wei Chen, Miaoli County (TW); Shih-Jen Liu, Miaoli County (TW); Pele Choi-Sing Chong, Miaoli County (TW)

(73) Assignee: National Health Research Institutes, Zhunan Town (TW)

( * ) Notice: Subject to any disclaimer, the term of this patent is extended or adjusted under 35 U.S.C. 154(b) by 643 days.

(21) Appl. No.: 12/820,264

(22) Filed: Jun. 22, 2010

(65) Prior Publication Data

US 2010/0322953 A1   Dec. 23, 2010

Related U.S. Application Data

(60) Provisional application No. 61/219,301, filed on Jun. 22, 2009.

(51) Int. Cl.
*A61K 39/00* (2006.01)
*A61K 38/00* (2006.01)

(52) U.S. Cl.
USPC .................................. 424/185.1; 424/93.1

(58) Field of Classification Search
None
See application file for complete search history.

(56) References Cited

U.S. PATENT DOCUMENTS

| | | | |
|---|---|---|---|
| 4,745,069 A | 5/1988 | Mayne et al. | |
| 5,942,236 A | 8/1999 | Lobet et al. | |
| 6,013,258 A | 1/2000 | Urban et al. | |
| 6,183,746 B1 | 2/2001 | Urban et al. | |
| 6,361,966 B1 | 3/2002 | Walker et al. | |
| 6,538,118 B1 | 3/2003 | Huebner et al. | |
| 6,582,704 B2 | 6/2003 | Urban et al. | |
| 6,936,263 B2 | 8/2005 | Revets et al. | |
| 7,097,843 B2 | 8/2006 | Urban et al. | |
| 7,235,243 B2 | 6/2007 | Becker et al. | |
| 7,314,629 B2 | 1/2008 | Zagury et al. | |
| 7,569,225 B2 | 8/2009 | Jackson et al. | |
| 7,833,776 B2 | 11/2010 | Leng et al. | |
| 2005/0276813 A1 | 12/2005 | Muhlradt et al. | |
| 2005/0281835 A1 | 12/2005 | Yang | |
| 2009/0074781 A1 | 3/2009 | Chen et al. | |
| 2009/0081253 A1 | 3/2009 | Hanon et al. | |
| 2009/0176273 A1 | 7/2009 | Leng et al. | |
| 2009/0221499 A1 | 9/2009 | Leng et al. | |
| 2010/0303849 A1 | 12/2010 | Chen et al. | |
| 2010/0322953 A1 | 12/2010 | Leng et al. | |
| 2012/0041179 A1 | 2/2012 | Hsieh et al. | |

FOREIGN PATENT DOCUMENTS

| | | |
|---|---|---|
| CA | 2183146 | 8/1995 |
| CA | 2706101 | 6/2009 |
| CN | 1793335 | 6/2006 |
| EP | 1612218 | 1/2006 |
| EP | 2058002 | 5/2009 |
| JP | 2008-113608 | 5/2008 |
| WO | WO 92/05248 | 4/1992 |
| WO | WO 92-16636 | 10/1992 |
| WO | WO 99/10357 | 3/1999 |
| WO | WO 99/57280 | 11/1999 |
| WO | WO01/00790 | 1/2001 |
| WO | WO 2004/052395 | 6/2004 |
| WO | WO 2007/119896 | 10/2007 |
| WO | 2008/049329 | 5/2008 |
| WO | WO 2008/079372 | 7/2008 |
| WO | WO 2010/148496 | 12/2010 |
| WO | WO 01/29236 | 4/2011 |

OTHER PUBLICATIONS

Sung, et al. Biochemical characterizations of *Escherichia coli*—expressed protective antigen Ag473 of Neisseria meningitides group B., *Vaccine*. vol. 28(51) Nov. 29, 2010, pp. 8175-8182.
ExPASy—PeptideCutter http://web.expasy.ort/cgi-bin/peptide_cutter/peptidecutter.pl (Accessed Mar. 7, 2012).
Shu, et al. Core Structure of the Outer membrane Lipoprotein from *Escherichia coli* at 1.9A Resolution, (2000) vol. 299, pp. 1101-11112.
Rezwan, et al. "Lipoprotein synthesis in mycobacteria" *Microbiology*. Mar. 2007, vol. 153, pp. 652-658.
Wikman, et al. General strategies for efficient adjuvant incorporation of recombinant subunit immunogents. *Vaccine*. (2005), vol. 23, pp. 2331-2335.
Masconi, et al. "Structural Basis for the Immunogenic Properties of the Meningocòccal Vaccine Candidate LP2086" The Journal of Biological Chemistry, vol. 284, No. 13, pp. 8738-8746 (Mar. 27, 2009).
Sivashanmugam, Arun, et al. "Practical protocols for production of very high yields of recombinant proteins using *Escherichia coli*" Protein Science vol. 18, pp. 936-948 (2009).
Chiung-Yi Huang et al. "Recombinant Lipidated HPV E7 Induces a TH-1-Biased Immune Response and Protective Immunity against Cervical Cancer in a Mouse Model," PLOS ONE, 7(7) e40970-e40970 (2012).
Chen, et al. "A novel technology for the production of a heterologous lipoprotein immuongen in high yield has implications for the field of vaccine design." Vaccine 27, pp. 1400-1409, Feb. 2009.
Liu, et al. "Structure of the Human Papillomavirus E7 Oncoprotein and its Mechanism for Inactivation of the Retinoblastoma Tumor Suppressor", J. Biol. Chem., Jan. 2006. vol. 281, pp. 578-586.
International Search Report and Written Opinion issued in PCT/CA2010/000960 dated Oct. 14, 2010, 19 pages.
Cote-Sierra, et al. "A New Membrane-Bound Oprl Lipoprotein Expression Vector High Production of Heterologous Fusion Proteins in Gram (-) Bacteria and the Implications for Oral Vaccination" GENE (1998) vol. 221, pp. 25-34.

(Continued)

*Primary Examiner* — Bao Li
(74) *Attorney, Agent, or Firm* — Cesari and McKenna, LLP

(57) ABSTRACT

Disclosed are polypeptides and fusion proteins. Also disclosed are related immunotherapeutic compositions and methods.

22 Claims, 6 Drawing Sheets

(56) References Cited

OTHER PUBLICATIONS

Crill, Wayne D., et al. "Monoclonal Antibodies That Blind to Domain III of Dengue Virus E Glycoprotein are the Most Efficient Blockers of Virus Adsorption to Vero Cells" *Journal of Virology* (Aug. 2001) pp. 7769-7773.

Chen, W., et al. "Induction of cytotoxic T-lymphocytes and antitumor activity by a liposomal lipopeptide vaccine" *Mol. Pharm.* vol. 5, No. 3, (2008) pp. 464-471.

Jackson, D.C., et al. "A totally synthetic vaccine of generic structure that targets Toll-like receptor 2 on dendritic cells and promotes antibody or cytotoxic T cell responses" *Proc. Natl. Acad. Sci. USA* vol. 101, No. 43 (2004) pp. 1540-15445.

Chen, W., et al. "Induction of cytotoxic T-lymphocytes and antitumor activity by a liposomal lipopeptide vaccine" *Mol. Pharm.* vol. 5, No. 3 (2008) pp. 464-471.

Babaeipour, Valiollah, et al. "Enhancement of human granulocyte-colony stimulating factor production in recombinant *E. coli* using batch cultivation" Bioprocess Biosyst Eng (2010) pp. 591-598.

Cullen et al., "Construction and Evaluation of a Plasmid Vector for the Expression of Recombinant Lipoproteins in *Escherichia coli*," Plasmid 49: 18-29 (2003).

De et al., "Purification and Characterization of *Streptococcis pneumoniae* palmitoylated and pneumococcal surface adhesion A expressed in *Escherichia coli*," Vaccine: 18: 1811-1821 (2000).

Dumon-Seignovert et al., The toxicity of recombinant proteins in *Escherichia coli*: a comparison of overexpression in BL21 (DE3), C41 (DE3), and C43(DE3)., Protein Expression and Purification, vol. 37, Issue 1, Sep. 2004, pp. 203-206.

*E. coli* genotypes (last viewed on Feb. 1, 2011).

Esche, U. v.d. et al. Immunostimulation by bacterial components: I. Activation of macrophages and enhancement of genetic immunization by the lipopeptide P3CSK4. Intl. 1. Immunopharm. Dec. 2000. vol. 22, pp. 1093-1102.

Green et al., The e(P4) Outer membrane Protein of Haemophilus influenzae: biologic activity of Anti-e Serum and Cloning and Sequencing of the Structural Gene., Infection and Immunity, 1991, vol. 59, pp. 3191-3198.

Hsu, C-A. et at. Immunoproteomic identification of the hypothetical protein NMB1468 as a novel lipoprotein ubiquitous in Neisseria meningitidis with vaccine potential. Proteomics. 2008. vol. 8, pp. 2115-2125.

Kamalakkannan et al., "Bacterial Lipid Modification of Proteins for Novel Protein Engineering Applications," Protein, Engineering, Design & Selection 17(10): 721-729 (2004).

Legrain et al., "Production of Lipidated Meningococcal Transferrin Binding Protein 2 in *Escherichia coli*" Protein Expression and Purification 6:570-578 (1995).

Klein et al., "Molecular Analysis and Nucleotide Sequence of the envCD operon of *Escherichia coli*," Mol. Ben. Genet. 230: 230-240 (1991).

Chiung-Yi Huang. "Potential Treatment of Human Papillomavirus Associated Tumors Using Recombinant Inactive-E7 Lipoproteins." Electronic Theses & Dissertations Services; Master Programs of Life Sciences, Aug. 24, 2009. pp. 1-5.

Chen et al. "A novel technology for the production of a heterologous lipoprotein immunogen in high yield has implications for the field of vaccine design." Vaccine, vol. 27, 2009. pp. 1400-1409.

Steller et al. "Cell-mediated Immunological Responses in Cervical and Vaginal Cancer Patients Immunized with a Lipidated Epitope of Human Papillomavirus Type 16 E7." Clinical Cancer Research, vol. 4, Sep. 1998, pp. 2103-2109.

Figure 1
A

```
Met His Gly Asp Thr Pro Thr Leu His Glu Tyr Met Leu Asp Leu Gln
1               5                   10                  15
Pro Glu Thr Thr Asp Leu Tyr Cys Tyr Glu Gln Leu Asn Asp Ser Ser
            20                  25                  30
Glu Glu Glu Asp Glu Ile  Asp Gly Pro Ala Gly Gln Ala Glu Pro Asp
        35                  40                  45
Arg Ala His Tyr Asn Ile Val Thr Phe Cys Cys Lys Cys Asp Ser Thr
        50                  55                  60
Leu Arg Leu Cys Val Gln Ser Thr His Val Asp Ile Arg Thr Leu Glu
65                  70                  75                  80
Asp Leu Leu Met Gly Thr Leu Gly Ile Val Cys Pro Ile Cys Ser Gln
                85                  90                  95
Lys Pro
```

B

```
Met His Gly Asp Thr Pro Thr Leu His Glu Tyr Met Leu Asp Leu Gln
1               5                   10                  15
Pro Glu Thr Thr Asp Leu Tyr Gly Tyr Gln Gln Leu Asn Asp Ser Ser
            20                  25                  30
Glu Glu Glu Asp Glu Ile  Asp Gly Pro Ala Gly Gln Ala Glu Pro Asp
        35                  40                  45
Arg Ala His Tyr Asn Ile Val Thr Phe Ala Ser Lys Ala Asp Ser Thr
        50                  55                  60
Leu Arg Leu Ser Val Gln Ser Thr His Val Asp Ile Arg Thr Leu Glu
65                  70                  75                  80
Asp Leu Leu Met Gly Thr Leu Gly Ile Val Ala Pro Ile Ala Ser Gln
                85                  90                  95
Lys Pro
```

Figure 2
A
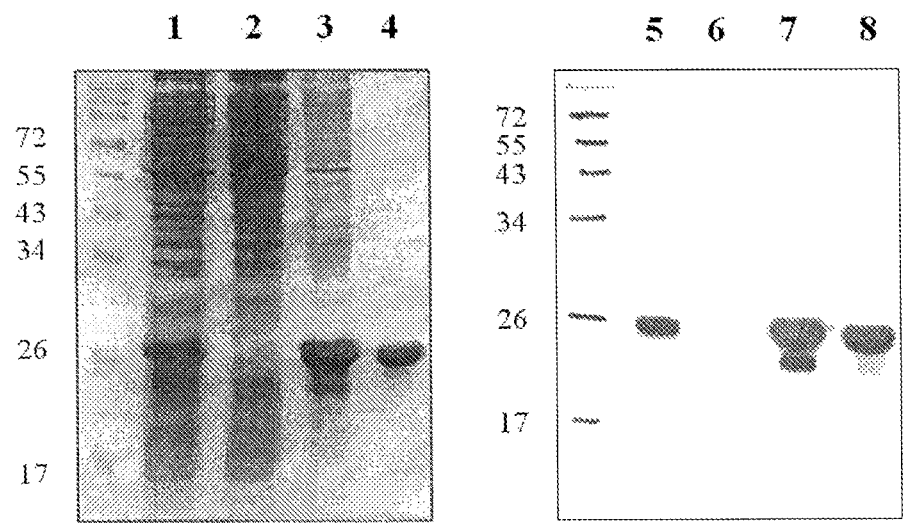
B
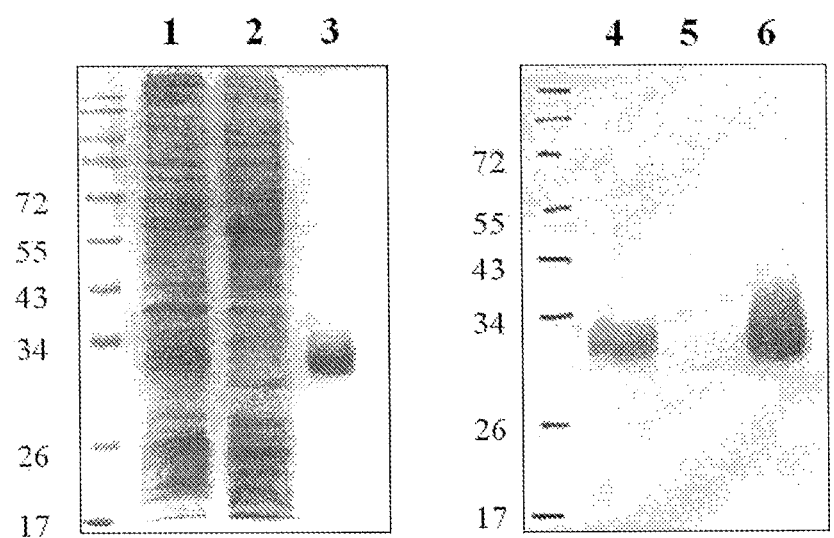

Figure 3
A
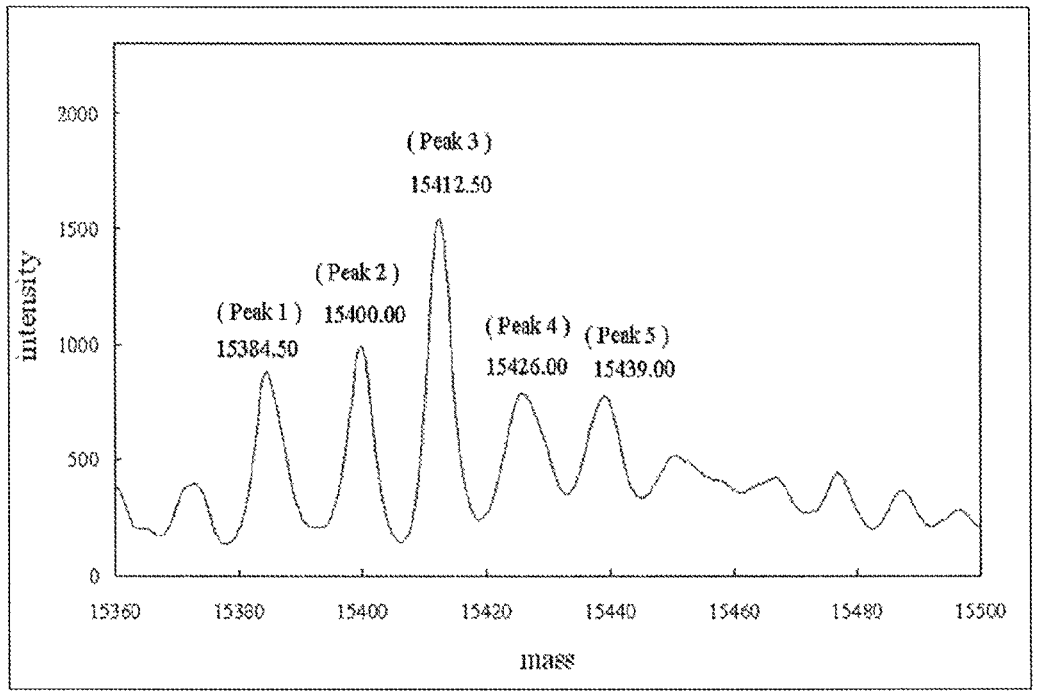
B
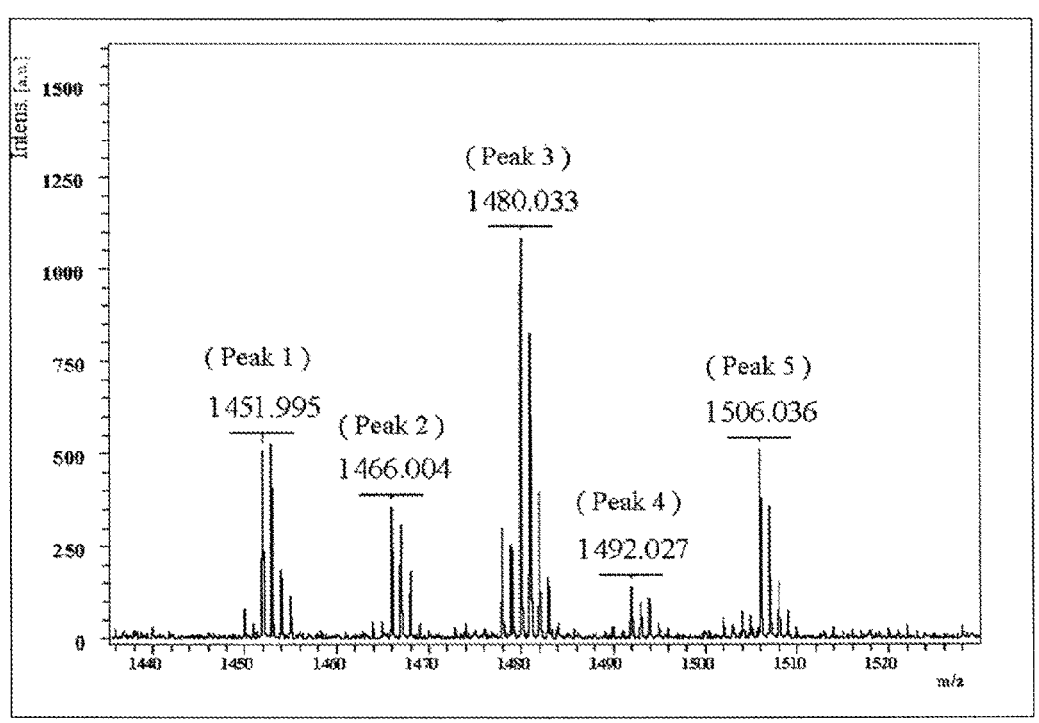

SEQUENCE LISTING

<160> NUMBER OF SEQ ID NOS: 33

<210> SEQ ID NO 1
<211> LENGTH: 98
<212> TYPE: PRT
<213> ORGANISM: human papillomavirus

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 2
<211> LENGTH: 98
<212> TYPE: PRT
<213> ORGANISM: human papillomavirus

<400> SEQUENCE: 2

Met His Gly Asp Thr Pro Thr Leu His Glu Tyr Met Leu Asp Leu Gln
1               5                   10                  15

Pro Glu Thr Thr Asp Leu Tyr Gly Tyr Gln Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Ala Ser Lys Ala Asp Ser Thr
        50                  55                  60

Leu Arg Leu Ser Val Gln Ser Thr His Val Asp Ile Arg Thr Leu Glu
65                  70                  75                  80

Asp Leu Leu Met Gly Thr Leu Gly Ile Val Ala Pro Ile Ala Ser Gln
                85                  90                  95

Lys Pro

<210> SEQ ID NO 3
<211> LENGTH: 35
<212> TYPE: DNA
<213> ORGANISM: Artificial sequence
<220> FEATURE:
<223> OTHER INFORMATION: Synthetic primer

<400> SEQUENCE: 3
ggaattccat atgcacggcg ataccccgac cctgc                            35

<210> SEQ ID NO 4
<211> LENGTH: 34
<212> TYPE: DNA
<213> ORGANISM: Artificial sequence
<220> FEATURE:
<223> OTHER INFORMATION: Synthetic primer

```
<400> SEQUENCE: 4
agagccgctc gagcggtttc tggctcgcaa tcgg                                34

<210> SEQ ID NO 5
<211> LENGTH: 32
<212> TYPE: DNA
<213> ORGANISM: Artificial sequence
<220> FEATURE:
<223> OTHER INFORMATION: Synthetic primer

<400> SEQUENCE: 5
cgcggatcca tgcacggcga taccccgacc ct                                  32

<210> SEQ ID NO 6
<211> LENGTH: 34
<212> TYPE: DNA
<213> ORGANISM: Artificial sequence
<220> FEATURE:
<223> OTHER INFORMATION: Synthetic primer

<400> SEQUENCE: 6
agagccgctc gagcggtttc tggctcgcaa tcgg                                34

<210> SEQ ID NO 7
<211> LENGTH: 121
<212> TYPE: PRT
<213> ORGANISM: Neisseria Mengitidis

<400> SEQUENCE: 7

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Th

```
<210> SEQ ID NO 9
<211> LENGTH: 23
<212> TYPE: PRT
<213> ORGANISM: Artificial sequence
<220> FEATURE:
<223> OTHER INFORMATION: A fragment (aa 18-40) of Ag473, a Neisseria
      Mengitidis lipoprotein

<400> SEQUENCE: 9

Ser Gln Glu Ala Lys Gln Glu Val Lys Glu Ala Val Gln Ala Val Glu
1               5                   10                  15

Ser Asp Val Lys Asp Thr Ala
            20

<210> SEQ ID NO 10
<211> LENGTH: 31
<212> TYPE: PRT
<213> ORGANISM: Artificial sequence
<220> FEATURE:
<223> OTHER INFORMATION: A fragment (aa 41-71) of Ag473, a Neisseria
      Mengitidis lipoprotein

<400> SEQUENCE: 10

Ala Ser Ala Ala Glu Ser Ala Ala Ser Ala Val Glu Glu Ala Lys Asp
1               5                   10                  15

Gln Val Lys Asp Ala Ala Ala Asp Ala Lys Ala Ser Ala Glu Glu
            20                  25                  30

<210> SEQ ID NO 11
<211> LENGTH: 50
<212> TYPE: PRT
<213> ORGANISM: Artificial sequence
<220> FEATURE:
<223> OTHER INFORMATION: A fragment (aa 72-121) of Ag473, a Neisseria
      Mengitidis lipoprotein

<400> SEQUENCE: 11

Ala Val Thr Glu Ala Lys Glu Ala Val Thr Glu Ala Lys Glu Ala Val
1               5                   10                  15

Thr Glu Ala Lys Glu Ala Val Thr Glu Ala Ala Lys Asp Thr Leu Asn
            20                  25                  30

Lys Ala Ala Asp Ala Thr Gln Glu Ala Ala Asp Lys Met Lys Asp Ala
        35                  40                  45

Ala Lys
    50

<210> SEQ ID NO 12
<211> LENGTH: 40
<212> TYPE: PRT
<213> ORGANISM: Artificial sequence
<220> FEATURE:
<223> OTHER INFORMATION: A fragment (aa 1-40) of Ag473, a Neisseria
      Mengitidis lipoprotein

<400> SEQUENCE: 12

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala
        35                  40
```

```
<210> SEQ ID NO 13
<211> LENGTH: 294
<212> TYPE: DNA
<213> ORGANISM: human papillomavirus

<400> SEQUENCE: 13
atgcatggcg ataccccgac cctgcatgaa tatatgctgg atctgcagcc ggaaaccacc        60
gatctgtatg gctatcagca gctgaacgat agcagcgaag aagaagatga aattgatggc       120
ccggcgggcc aggcggaacc ggatcgcgcg cattataaca ttgtgacctt tgcgagcaaa       180
gcggatagca ccctgcgcct gagcgtgcag agcacccatg tggatattcg caccctggaa       240
gatctgctga tgggcaccct gggcattgtg gcgccgattg cgagccagaa accg             294

<210> SEQ ID NO 14
<211> LENGTH: 140
<212> TYPE: PRT
<213> ORGANISM: Artificial sequence
<220> FEATURE:
<223> OTHER INFORMATION: rlipo-E7m fusion protein

<400> SEQUENCE: 14

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Gly Ser Met His Gly Asp Thr Pro
        35                  40                  45

Thr Leu His Glu Tyr Met Leu Asp Leu Gln Pro Glu Thr Thr Asp Leu
    50                  55                  60

Tyr Gly Tyr Gln Gln Leu Asn Asp Ser Ser Glu Glu Asp Glu Ile
65                  70                  75                  80

Asp Gly Pro Ala Gly Gln Ala Glu Pro Asp Arg Ala His Tyr Asn Ile
                85                  90                  95

Val Thr Phe Ala Ser Lys Ala Asp Ser Thr Leu Arg Leu Ser Val Gln
            100                 105                 110

Ser Thr His Val Asp Ile Arg Thr Leu Glu Asp Leu Leu Met Gly Thr
        115                 120                 125

Leu Gly Ile Val Ala Pro Ile Ala Ser Gln Lys Pro
    130                 135                 140

<210> SEQ ID NO 15
<211> LENGTH: 420
<212> TYPE: DNA
<213> ORGANISM: Artificial sequence
<220> FEATURE:
<223> OTHER INFORMATION: a DNA sequence coding rlipo-E7m fusion protein

<400> SEQUENCE: 15
atgaaaaaac tgctgattgc ggcgatgatg gcggcggcgc tggcggcgtg cagccaggaa        60
gcgaaacagg aagtgaaaga agcggtgcag gcggtggaaa gcgatgtgaa agataccgcg       120
ggatccatgc atggcgatac cccgaccctg catgaatata tgctggatct gcagccggaa       180
accaccgatc tgtatggcta tcagcagctg aacgatagca gcgaagaaga agatgaaatt       240
gatggcccgg cgggccaggc ggaaccggat cgtgcgcatt ataacattgt gacctttgcg       300
agcaaagcgg atagcaccct gcgtctgagc gtgcagagca cccatgtgga tattcgtacc       360
ctggaagatc tgctgatggg caccctgggc attgtggcgc cgattgcgag ccagaaaccg       420
```

-continued

```
<210> SEQ ID NO 16
<211> LENGTH: 404
<212> TYPE: PRT
<213> ORGANISM: human herpesvirus 4

<400> SEQUENCE: 16

Met Glu Arg Asp Leu Glu Arg Gly Pro Pro Gly Pro Arg Pro Pro
1               5                   10                  15

Leu Gly Pro Pro Leu Ser Ser Ile Gly Leu Ala Leu Leu Leu Leu
                20                  25                  30

Leu Leu Ala Leu Leu Phe Trp Leu Tyr Ile Val Met Ser Asp Trp Thr
            35                  40                  45

Gly Gly Ala Leu Leu Val Leu Tyr Ser Phe Ala Leu Met Leu Ile Ile
        50                  55                  60

Ile Ile Leu Ile Ile Phe Ile Phe Arg Arg Asp Leu Leu Cys Pro Leu
65                  70                  75                  80

Gly Gly Leu Gly Leu Leu Leu Met Ile Thr Leu Leu Ile Ala
                85                  90                  95

Leu Trp Asn Leu His Gly Gln Ala Leu Tyr Leu Gly Ile Val Leu Phe
                100                 105                 110

Ile Phe Gly Cys Leu Leu Val Leu Gly Leu Trp Ile Tyr Phe Leu Glu
            115                 120                 125

Ile Leu Trp Arg Leu Gly Ala Thr Leu Trp Gln Leu Leu Ala Phe Ile
        130                 135                 140

Leu Ala Phe Phe Leu Ala Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Met Ala Ile Leu Ile Trp Met Tyr Tyr His Gly Pro Arg His Thr
            180                 185                 190

Asp Glu His His His Asp Asp Ser Leu Pro His Pro Gln Gln Ala Thr
        195                 200                 205

Asp Asp Ser Ser His Glu Ser Asp Ser Asn Ser Asn Glu Gly Arg His
        210                 215                 220

His Leu Leu Val Ser Gly Ala Gly Asp Gly Pro Pro Leu Cys Ser Gln
225                 230                 235                 240

Asn Leu Gly Ala Pro Gly Gly Pro Asp Asn Gly Pro Gln Asp Pro
                245                 250                 255

Asp Asn Thr Asp Asp Asn Gly Pro Gln Asp Pro Asp Asn Thr Asp Asp
            260                 265                 270

Asn Gly Pro Gln Asp Pro Asp Asn Thr Asp Asn Gly Pro Gln Asp
        275                 280                 285

Pro Asp Asn Thr Asp Asp Asn Gly Pro Gln Asp Pro Asp Asn Thr Asp
        290                 295                 300

Asp Asn Gly Pro Gln Asp Pro Asp Asn Thr Asp Asn Gly Pro Gln
305                 310                 315                 320

Asp Pro Asp Asn Thr Asp Asn Gly Pro His Asp Pro Leu Pro His
                325                 330                 335

Asn Pro Ser Asp Ser Ala Gly Asn Asp Gly Pro Asn Leu Thr
                340                 345                 350

Glu Glu Val Ala Asn Lys Gly Gly Asp Arg Gly Pro Pro Ser Met Thr
            355                 360                 365

Asp Gly Gly Gly Gly Asp Pro His Leu Pro Thr Leu Leu Leu Gly Thr
        370                 375                 380
```

Ser Gly Ser Gly Gly Asp Asp Asp Pro His Gly Pro Val Gln Leu
385                 390                 395                 400

Ser Tyr Tyr Asp

<210> SEQ ID NO 17
<211> LENGTH: 497
<212> TYPE: PRT
<213> ORGANISM: human herpesvirus

<400> SEQUENCE: 17

Met Gly Ser Leu Glu Met Val Pro Met Gly Ala Gly Pro Ser Pro
1               5                   10                  15

Gly Gly Asp Pro Asp Gly Asp Gly Gly Asn Asn Ser Gln Tyr Pro
                20                  25                  30

Ser Ala Ser Gly Ser Ser Gly Asn Thr Pro Thr Pro Asn Asp Glu
            35                  40                  45

Glu Arg Glu Ser Asn Glu Glu Pro Pro Pro Tyr Glu Asp Pro Tyr
        50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
                100                 105                 110

Glu Glu Ala Gly Arg Gly Ser Met Asn Pro Val Cys Leu Pro Val Ile
            115                 120                 125

Val Ala Pro Tyr Leu Phe Trp Leu Ala Ala Ile Ala Ala Ser Cys Phe
130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
                180                 185                 190

Ala Ile Cys Leu Thr Trp Arg Ile Glu Asp Pro Pro Phe Asn Ser Leu
            195                 200                 205

Leu Phe Ala Leu Leu Ala Ala Ala Gly Gly Leu Gln Gly Ile Tyr Val
210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
                260                 265                 270

Thr Val Val Ser Met Thr Leu Leu Leu Leu Ala Phe Val Leu Trp Leu
            275                 280                 285

Ser Ser Pro Gly Gly Leu Gly Thr Leu Gly Ala Ala Leu Leu Thr Leu
290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

Leu Ile Cys Ser Ser Cys Ser Ser Cys Pro Leu Ser Lys Ile Leu Leu
                340                 345                 350

Ala Arg Leu Phe Leu Tyr Ala Leu Ala Leu Leu Leu Ala Ser Ala
            355                 360                 365

Leu Ile Ala Gly Gly Ser Ile Leu Gln Thr Asn Phe Lys Ser Leu Ser
    370                 375                 380

Ser Thr Glu Phe Ile Pro Asn Leu Phe Cys Met Leu Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Cys Leu Gly Gly Leu Leu Thr
            420                 425                 430

Met Val Ala Gly Ala Val Trp Leu Thr Val Met Thr Asn Thr Leu Leu
                435                 440                 445

Ser Ala Trp Ile Leu Thr Ala Gly Phe Leu Ile Phe Leu Ile Gly Phe
            450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
                485                 490                 495

Val

<210> SEQ ID NO 18
<211> LENGTH: 378
<212> TYPE: PRT
<213> ORGANISM: Human herpesvirus 4

<400> SEQUENCE: 18

Met Asn Pro Val Cys Leu Pro Val Ile Val Ala Pro Tyr Leu Phe Trp
1               5                   10                  15

Leu Ala Ala Ile Ala Ala Ser Cys Phe Thr Ala Ser Val Ser Thr Val
                20                  25                  30

Val Thr Ala Thr Gly Leu Ala Leu Ser Leu Leu Leu Leu Ala Ala Val
            35                  40                  45

Ala Ser Ser Tyr Ala Ala Ala Gln Arg Lys Leu Leu Thr Pro Val Thr
50                  55                  60

Val Leu Thr Ala Val Val Thr Phe Phe Ala Ile Cys Leu Thr Trp Arg
65                  70                  75                  80

Ile Glu Asp Pro Pro Phe Asn Ser Leu Leu Phe Ala Leu Leu Ala Ala
                85                  90                  95

Ala Gly Gly Leu Gln Gly Ile Tyr Val Leu Val Met Leu Val Leu Leu
                100                 105                 110

Ile Leu Ala Tyr Arg Arg Arg Trp Arg Arg Leu Thr Val Cys Gly Gly
            115                 120                 125

Ile Met Phe Leu Ala Cys Val Leu Val Leu Ile Val Asp Ala Val Leu
        130                 135                 140

Gln Leu Ser Pro Leu Leu Gly Ala Val Thr Val Val Ser Met Thr Leu
145                 150                 155                 160

Leu Leu Leu Ala Phe Val Leu Trp Leu Ser Ser Pro Gly Gly Leu Gly
                165                 170                 175

Thr Leu Gly Ala Ala Leu Leu Thr Leu Ala Ala Ala Leu Ala Leu Leu
            180                 185                 190

Ala Ser Leu Ile Leu Gly Thr Leu Asn Leu Thr Thr Met Phe Leu Leu
        195                 200                 205

Met Leu Leu Trp Thr Leu Val Val Leu Leu Ile Cys Ser Ser Cys Ser
    210                 215                 220

```
Ser Cys Pro Leu Ser Lys Ile Leu Ala Arg Leu Phe Leu Tyr Ala
225                 230                 235                 240

Leu Ala Leu Leu Leu Leu Ala Ser Ala Leu Ile Ala Gly Gly Ser Ile
            245                 250                 255

Leu Gln Thr Asn Phe Lys Ser Leu Ser Ser Thr Glu Phe Ile Pro Asn
        260                 265                 270

Leu Phe Cys Met Leu Leu Leu Ile Val Ala Gly Ile Leu Phe Ile Leu
    275                 280                 285

Ala Ile Leu Thr Glu Trp Gly Ser Gly Asn Arg Thr Tyr Gly Pro Val
290                 295                 300

Phe Met Cys Leu Gly Gly Leu Leu Thr Met Val Ala Gly Ala Val Trp
305                 310                 315                 320

Leu Thr Val Met Ser Asn Thr Leu Leu Ser Ala Trp Ile Leu Thr Ala
            325                 330                 335

Gly Phe Leu Ile Phe Leu Ile Gly Phe Ala Leu Phe Gly Val Ile Arg
        340                 345                 350

Cys Cys Arg Tyr Cys Cys Tyr Tyr Cys Leu Thr Leu Glu Ser Glu Glu
    355                 360                 365

Arg Pro Pro Thr Pro Tyr Arg Asn Thr Val
370                 375

<210> SEQ ID NO 19
<211> LENGTH: 886
<212> TYPE: PRT
<213> ORGANISM: Human herpesvirus 4

<400> SEQUENCE: 19

Met Glu Ala Ala Leu Leu Val Cys Gln Tyr Thr Ile Gln Ser Leu Ile
1               5                   10                  15

Gln Leu Thr Arg Asp Asp Pro Gly Phe Phe Asn Val Glu Ile Leu Glu
            20                  25                  30

Phe Pro Phe Tyr Pro Ala Cys Asn Val Cys Thr Ala Asp Val Asn Ala
        35                  40                  45

Thr Ile Asn Phe Asp Val Gly Gly Lys Lys His Lys Leu Asn Leu Asp
50                  55                  60

Phe Gly Leu Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Ile Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
210                 215                 220
```

-continued

```
Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
            245                 250                 255

Gly Thr Gly Tyr Ala Tyr Ser Leu Arg Leu Thr Pro Arg Pro Val Ser
        260                 265                 270

Arg Phe Leu Gly Asn Asn Ser Ile Leu Tyr Val Phe Tyr Ser Gly Asn
    275                 280                 285

Gly Pro Lys Ala Ser Gly Gly Asp Tyr Cys Ile Gln Ser Asn Ile Val
        290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
            325                 330                 335

Thr Ser Glu Asp Ala Asn Ser Pro Asn Val Thr Val Thr Ala Phe Trp
        340                 345                 350

Ala Trp Pro Asn Asn Thr Glu Thr Asp Phe Lys Cys Lys Trp Thr Leu
    355                 360                 365

Thr Ser Gly Thr Pro Ser Gly Cys Glu Asn Ile Ser Gly Ala Phe Ala
370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
            405                 410                 415

His Lys Val Ile Phe Ser Lys Ala Pro Glu Ser Thr Thr Thr Ser Pro
        420                 425                 430

Thr Leu Asn Thr Thr Gly Phe Ala Ala Pro Asn Thr Thr Thr Gly Leu
    435                 440                 445

Pro Ser Ser Thr His Val Pro Thr Asn Leu Thr Ala Pro Ala Ser Thr
450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Arg Asp
            485                 490                 495

Asn Gly Thr Glu Ser Lys Ala Pro Asp Met Thr Ser Pro Thr Ser Ala
        500                 505                 510

Val Thr Thr Pro Thr Pro Asn Ala Thr Ser Pro Thr Pro Ala Val Thr
    515                 520                 525

Thr Pro Thr Pro Asn Ala Thr Ser Pro Thr Leu Gly Lys Thr Ser Pro
530                 535                 540

Thr Ser Ala Val Thr Thr Pro Thr Pro Asn Ala Thr Ser Pro Thr Pro
545                 550                 555                 560

Ala Val Thr Thr Pro Thr Pro Asn Ala Thr Ile Pro Thr Leu Gly Lys
            565                 570                 575

Thr Ser Pro Thr Ser Ala Val Thr Thr Pro Thr Pro Asn Ala Thr Ser
        580                 585                 590

Pro Thr Val Gly Glu Thr Ser Pro Gln Ala Asn Thr Thr Asn His Thr
    595                 600                 605

Leu Gly Gly Thr Ser Ser Thr Pro Val Val Thr Ser Pro Pro Lys Asn
610                 615                 620

Ala Thr Ser Ala Val Thr Thr Gly Gln His Asn Ile Thr Ser Ser Ser
625                 630                 635                 640

Thr Ser Ser Met Ser Leu Arg Pro Ser Ser Ile Ser Glu Thr Leu Ser
            645                 650                 655
```

```
Pro Ser Thr Ser Asp Asn Ser Thr Ser His Met Pro Leu Leu Thr Ser
            660                 665                 670

Ala His Pro Thr Gly Gly Glu Asn Ile Thr Gln Val Thr Pro Ala Ser
            675                 680                 685

Thr Ser Thr His His Val Ser Thr Ser Ser Pro Ala Pro Arg Pro Gly
            690                 695                 700

Thr Thr Ser Gln Ala Ser Gly Pro Gly Asn Ser Ser Thr Ser Thr Lys
705                 710                 715                 720

Pro Gly Glu Val Asn Val Thr Lys Gly Thr Pro Lys Asn Ala Thr
                    725                 730                 735

Ser Pro Gln Ala Pro Ser Gly Gln Lys Thr Ala Val Pro Thr Val Thr
                    740                 745                 750

Ser Thr Gly Gly Lys Ala Asn Ser Thr Thr Gly Gly Lys His Thr Thr
            755                 760                 765

Gly His Gly Ala Arg Thr Ser Thr Glu Pro Thr Thr Asp Tyr Gly Gly
            770                 775                 780

Asp Ser Thr Thr Pro Arg Thr Arg Tyr Asn Ala Thr Thr Tyr Leu Pro
785                 790                 795                 800

Pro Ser Thr Ser Ser Lys Leu Arg Pro Arg Trp Thr Phe Thr Ser Pro
                    805                 810                 815

Pro Val Thr Thr Ala Gln Ala Thr Val Pro Val Pro Pro Thr Ser Gln
            820                 825                 830

Pro Arg Phe Ser Asn Leu Ser Met Leu Val Leu Gln Trp Ala Ser Leu
            835                 840                 845

Ala Val Leu Thr Leu Leu Leu Leu Val Met Ala Asp Cys Ala Phe
850                 855                 860

Arg Arg Asn Leu Ser Thr Ser His Thr Tyr Thr Thr Pro Pro Tyr Asp
865                 870                 875                 880

Asp Ala Glu Thr Tyr Val
                885

<210> SEQ ID NO 20
<211> LENGTH: 454
<212> TYPE: PRT
<213> ORGANISM: Human herpesvirus 4

<400> SEQUENCE: 20

Met Pro Thr Tyr Tyr Leu Ala Leu His Gly Gly Gln Ser Tyr Asn Leu
1               5                   10                  15

Ile Val Asp Thr Asp Met Ser Gly Asn Pro Ser Leu Ser Val Ile Pro
                20                  25                  30

Thr Asn Pro Tyr Gln Glu Gln Leu Ser Asn Asn Pro Leu Ile Gln Leu
            35                  40                  45

Gln Ile Val Val Gly Glu Asn Thr Gly Ala Pro Ala Pro Gln Pro
    50                  55                  60

Pro Pro Pro Pro Pro Pro Pro Pro Glu Arg Arg Asp Ala Trp
65                  70                  75                  80

Thr Gln Glu Pro Leu Pro Leu Asp Met Asn Pro Leu Gly Ser Asp Ala
            85                  90                  95

Ser Gln Gly Pro Leu Ala Ser Ser Ile Arg Met Leu Cys Met Ala Gln
            100                 105                 110

Tyr Leu Leu Arg Asn Ala Arg Gly Gln Gln Gly Leu Leu Arg Pro Leu
            115                 120                 125

Gly Pro Gln Thr Arg Ser Gln Val Thr Leu Glu Arg Gln Pro Val His
            130                 135                 140
```

-continued

Asn Pro Arg Gln Glu Ala Pro Ile Ile Leu Leu Gln Ser Pro Ala Pro
145                 150                 155                 160

Pro Arg Phe Thr Pro Val Pro Met Val Ala Leu Gly His Thr Leu Gln
            165                 170                 175

Pro Thr Pro Pro Pro Arg Pro Thr Leu Pro Gln Pro Arg Ile Pro Leu
        180                 185                 190

Ile Ile Pro Pro Arg His Thr Asn Gln Pro Ala Thr Thr Pro Pro Thr
    195                 200                 205

Ala Pro Gln Arg Leu Thr Leu Gly His Gln Leu Ser Leu Pro Pro His
210                 215                 220

Pro Pro Pro His Gln Ser Thr Pro His Cys Ser Ser Asp Ser Thr Gly
225                 230                 235                 240

Leu Pro Pro Pro Thr Ser Tyr Ser Ile Pro Ser Met Thr Leu Ser
            245                 250                 255

Pro Glu Pro Leu Pro Pro Ala Ala Pro Ala His Pro Leu Pro Gly
                260                 265                 270

Val Ile Tyr Asp Gln Gln Ala Leu Pro Pro Thr Pro Gly Pro Pro Trp
        275                 280                 285

Trp Pro Pro Val Arg Asp Pro Thr Pro Thr Gln Thr Pro Pro Thr
    290                 295                 300

Asn Thr Lys Gln Gly Pro Asp Gln Gly Gln Gly Arg Gly Arg Trp Arg
305                 310                 315                 320

Gly Arg Gly Arg Ser Lys Gly Arg Gly Arg Met His Lys Leu Pro Glu
            325                 330                 335

Pro Arg Arg Pro Gly Pro Asp Thr Ser Ser Pro Ser Met Pro Gln Leu
        340                 345                 350

Ser Pro Val Val Ser Leu His Gln Gly Gln Gly Pro Glu Asn Ser Pro
        355                 360                 365

Thr Pro Gly Pro Ser Thr Ala Gly Pro Val Cys Arg Val Thr Pro Ser
370                 375                 380

Ala Thr Pro Asp Ile Ser Pro Ile His Glu Pro Glu Ser Ser Asp Ser
385                 390                 395                 400

Glu Glu Pro Pro Phe Leu Phe Pro Ser Asp Trp Tyr Pro Pro Thr Leu
            405                 410                 415

Glu Pro Ala Glu Leu Asp Glu Ser Trp Glu Gly Ile Phe Glu Thr Thr
        420                 425                 430

Glu Ser His Ser Ser Asp Glu Glu Asn Val Gly Gly Pro Ser Lys Arg
        435                 440                 445

Pro Arg Thr Ser Thr Gln
    450

<210> SEQ ID NO 21
<211> LENGTH: 992
<212> TYPE: PRT
<213> ORGANISM: Human herpesvirus 4

<400> SEQUENCE: 21

Met Glu Ser Phe Glu Gly Gln Gly Asp Ser Arg Gln Ser Pro Asp Asn
1               5                   10                  15

Glu Arg Gly Asp Asn Val Gln Thr Thr Gly Glu His Asp Gln Asp Pro
            20                  25                  30

Gly Pro Gly Pro Pro Ser Ser Gly Ala Ser Glu Arg Leu Val Pro Glu
        35                  40                  45

Glu Ser Tyr Ser Arg Asp Gln Gln Pro Trp Gly Gln Ser Arg Gly Asp
    50                  55                  60

-continued

```
Glu Asn Arg Gly Trp Met Gln Arg Ile Arg Arg Arg Arg Arg Arg
 65                  70                  75                  80

Ala Ala Leu Ser Gly His Leu Leu Asp Thr Glu Asp Asn Val Pro Pro
             85                  90                  95

Trp Leu Pro Pro His Asp Ile Thr Pro Tyr Thr Ala Arg Asn Ile Arg
            100                 105                 110

Asp Ala Ala Cys Arg Ala Val Lys Gln Ser His Leu Gln Ala Leu Ser
            115                 120                 125

Asn Leu Ile Leu Asp Ser Gly Leu Asp Thr Gln His Ile Leu Cys Phe
130                 135                 140

Val Met Ala Ala Arg Gln Arg Leu Gln Asp Ile Arg Arg Gly Pro Leu
145                 150                 155                 160

Val Ala Glu Gly Gly Val Gly Trp Arg His Trp Leu Leu Thr Ser Pro
                165                 170                 175

Ser Gln Ser Trp Pro Met Gly Tyr Arg Thr Ala Thr Leu Arg Thr Leu
            180                 185                 190

Thr Pro Val Pro Asn Arg Val Gly Ala Asp Ser Ile Met Leu Thr Ala
            195                 200                 205

Thr Phe Gly Cys Gln Asn Ala Ala Arg Thr Leu Asn Thr Phe Ser Ala
210                 215                 220

Thr Val Trp Thr Pro Pro His Ala Gly Pro Arg Glu Gln Glu Arg Tyr
225                 230                 235                 240

Ala Arg Glu Ala Glu Val Arg Phe Leu Arg Gly Lys Trp Gln Arg Arg
                245                 250                 255

Tyr Arg Arg Ile Tyr Asp Leu Ile Glu Leu Cys Gly Ser Leu His His
            260                 265                 270

Ile Trp Gln Asn Leu Leu Gln Thr Glu Glu Asn Leu Leu Asp Phe Val
            275                 280                 285

Arg Phe Met Gly Val Met Ser Ser Cys Asn Asn Pro Ala Val Asn Tyr
290                 295                 300

Trp Phe His Lys Thr Ile Gly Asn Phe Lys Pro Tyr Tyr Pro Trp Asn
305                 310                 315                 320

Ala Pro Pro Asn Glu Asn Pro Tyr His Ala Arg Arg Gly Ile Lys Glu
                325                 330                 335

His Val Ile Gln Asn Ala Phe Arg Lys Ala Gln Ile Gln Gly Leu Ser
            340                 345                 350

Met Leu Ala Thr Gly Gly Glu Pro Arg Gly Asp Ala Thr Ser Glu Thr
            355                 360                 365

Ser Ser Asp Glu Asp Thr Gly Arg Gln Gly Ser Asp Val Glu Leu Glu
370                 375                 380

Ser Ser Asp Asp Glu Leu Pro Tyr Ile Asp Pro Asn Met Glu Pro Val
385                 390                 395                 400

Gln Gln Arg Pro Val Met Phe Val Ser Arg Val Pro Ala Lys Lys Pro
                405                 410                 415

Arg Lys Leu Pro Trp Pro Thr Pro Lys Thr His Pro Val Lys Arg Thr
            420                 425                 430

Asn Val Lys Thr Ser Asp Arg Ser Asp Lys Ala Glu Ala Gln Ser Thr
            435                 440                 445

Pro Glu Arg Pro Gly Pro Ser Glu Gln Ser Ser Val Thr Val Glu Pro
450                 455                 460

Ala His Pro Thr Pro Val Glu Met Pro Met Val Ile Leu His Gln Pro
465                 470                 475                 480

Pro Pro Val Pro Lys Pro Val Pro Val Lys Pro Thr Pro Pro Pro Ser
                485                 490                 495
```

```
Arg Arg Arg Arg Gly Ala Cys Val Val Tyr Asp Asp Val Ile Glu
            500                 505                 510
Val Ile Asp Val Glu Thr Thr Glu Asp Ser Ser Val Ser Gln Pro
        515                 520                 525
Asn Lys Pro His Arg Lys His Gln Asp Gly Phe Gln Arg Ser Gly Arg
    530                 535                 540
Arg Gln Lys Arg Ala Ala Pro Pro Thr Val Ser Pro Ser Asp Thr Gly
545                 550                 555                 560
Pro Pro Ala Val Gly Pro Ala Ala Gly Pro Ala Ala Gly Pro
                565                 570                 575
Pro Ala Ala Gly Pro Ala Ala Gly Pro Ala Ala Gly Pro
            580                 585                 590
Ala Ala Gly Pro Arg Ile Leu Ala Pro Leu Ser Ala Gly Pro Pro Ala
        595                 600                 605
Ala Gly Pro His Ile Val Thr Pro Pro Ser Ala Arg Pro Arg Ile Met
    610                 615                 620
Ala Pro Pro Val Val Arg Met Phe Met Arg Glu Arg Gln Leu Pro Gln
625                 630                 635                 640
Ser Thr Gly Arg Lys Pro Gln Cys Phe Trp Glu Met Arg Ala Gly Arg
                645                 650                 655
Glu Ile Thr Gln Met Gln Gln Glu Pro Ser Ser His Leu Gln Ser Ala
            660                 665                 670
Thr Gln Pro Thr Thr Pro Arg Pro Ser Trp Ala Pro Ser Val Cys Ala
        675                 680                 685
Leu Ser Val Met Asp Ala Gly Lys Ala Gln Pro Ile Glu Ser Ser His
    690                 695                 700
Leu Ser Ser Met Ser Pro Thr Gln Pro Ile Ser His Glu Glu Gln Pro
705                 710                 715                 720
Arg Tyr Glu Asp Pro Asp Ala Pro Leu Asp Leu Ser Leu His Pro Asp
                725                 730                 735
Val Ala Ala Gln Pro Ala Pro Gln Ala Pro Tyr Gln Gly Tyr Gln Glu
            740                 745                 750
Pro Pro Ala Pro Gln Ala Pro Tyr Gln Gly Tyr Gln Glu Pro Pro
        755                 760                 765
Pro Gln Ala Pro Tyr Gln Gly Tyr Gln Glu Pro Pro Ala His Gly Leu
    770                 775                 780
Gln Ser Ser Ser Tyr Pro Gly Tyr Ala Gly Pro Trp Thr Pro Arg Ser
785                 790                 795                 800
Gln His Pro Cys Tyr Arg His Pro Trp Ala Pro Trp Ser Gln Asp Pro
                805                 810                 815
Val His Gly His Thr Gln Gly Pro Trp Asp Pro Arg Ala Pro His Leu
            820                 825                 830
Pro Pro Gln Trp Asp Gly Ser Ala Gly His Gly Gln Asp Gln Val Ser
        835                 840                 845
Gln Phe Pro His Leu Gln Ser Glu Thr Gly Pro Pro Arg Leu Gln Leu
    850                 855                 860
Ser Leu Val Pro Leu Val Ser Ser Ala Pro Ser Trp Ser Ser Pro
865                 870                 875                 880
Gln Pro Arg Ala Pro Ile Arg Pro Ile Pro Thr Arg Phe Pro Pro
                885                 890                 895
Pro Met Pro Leu Gln Asp Ser Met Ala Val Gly Cys Asp Ser Ser Gly
            900                 905                 910
Thr Ala Cys Pro Ser Met Pro Phe Ala Ser Asp Tyr Ser Gln Gly Ala
        915                 920                 925
```

```
Phe Thr Pro Leu Asp Ile Asn Ala Thr Thr Pro Lys Arg Pro Arg Val
            930                 935                 940

Glu Glu Ser Ser His Gly Pro Ala Arg Cys Ser Gln Ala Thr Ala Glu
945                 950                 955                 960

Ala Gln Glu Ile Leu Ser Asp Asn Ser Glu Ile Ser Val Phe Pro Lys
                965                 970                 975

Asp Ala Lys Gln Thr Asp Tyr Asp Ala Ser Thr Glu Ser Glu Leu Asp
            980                 985                 990

<210> SEQ ID NO 22
<211> LENGTH: 631
<212> TYPE: PRT
<213> ORGANISM: Hepatitis C virus

<400> SEQUENCE: 22

Ala Pro Ile Thr Ala Tyr Ala Gln Gln Thr Arg Gly Leu Leu Gly Cys
1               5                   10                  15

Ile Ile Thr Gly Leu Thr Gly Arg Asp Lys Asn Gln Val Glu Gly Glu
            20                  25                  30

Val Gln Ile Val Ser Thr Ala Ala Gln Thr Phe Leu Ala Thr Cys Ile
        35                  40                  45

Asn Gly Val Cys Trp Thr Val Tyr His Gly Ala Gly Thr Arg Thr Ile
50                  55                  60

Ala Ser Ser Lys Gly Pro Val Ile Gln Met Tyr Thr Asn Val Asp Gln
65                  70                  75                  80

Asp Leu Val Gly Trp Pro Ala Pro Gln Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Gly Arg Gly Ser Leu Leu Ser
        115                 120                 125

Pro Arg Pro Ile Ser Tyr Leu Lys Gly Ser Ser Gly Gly Pro Leu Leu
130                 135                 140

Cys Pro Ala Gly His Ala Val Gly Ile Phe Arg Ala Ala Val Cys Thr
145                 150                 155                 160

Arg Gly Val Ala Lys Ala Val Asp Phe Ile Pro Val Glu Gly Leu Glu
                165                 170                 175

Thr Thr Met Arg Ser Pro Val Phe Ser Asp Asn Ser Ser Pro Pro Ala
            180                 185                 190

Val Pro Gln Ser Tyr Gln Val Ala His Leu His Ala Pro Thr Gly Ser
        195                 200                 205

Gly Lys Ser Thr Lys Val Pro Ala Ala Tyr Ala Ala Gln Gly Tyr Lys
210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ser Pro Ile Thr Tyr Ser Thr Tyr Gly Lys
            260                 265                 270

Phe Leu Ala Asp Gly Gly Cys Ser Gly Ser Ala Tyr Asp Ile Ile Ile
        275                 280                 285

Cys Asp Glu Cys His Ser Thr Asp Ala Thr Ser Ile Leu Gly Ile Gly
290                 295                 300

Thr Val Leu Asp Gln Ala Glu Thr Ala Gly Ala Arg Leu Thr Val Leu
305                 310                 315                 320
```

```
Ala Thr Ala Thr Pro Pro Gly Ser Val Thr Val Pro His Pro Asn Ile
            325                 330                 335

Glu Glu Val Ala Leu Ser Thr Thr Gly Glu Ile Pro Phe Tyr Gly Lys
        340                 345                 350

Ala Ile Pro Leu Glu Ala Ile Lys Gly Gly Arg His Leu Ile Phe Cys
        355                 360                 365

His Ser Lys Lys Lys Cys Asp Glu Leu Ala Ala Lys Leu Val Ala Leu
    370                 375                 380

Gly Val Asn Ala Val Ala Tyr Tyr Arg Gly Leu Asp Val Ser Val Ile
385                 390                 395                 400

Pro Ala Ser Gly Asp Val Val Val Ala Thr Asp Ala Leu Met Thr
                405                 410                 415

Gly Phe Thr Gly Asp Phe Asp Ser Val Ile Asp Cys Asn Thr Cys Val
                420                 425                 430

Thr Gln Thr Val Asp Phe Ser Leu Asp Pro Thr Phe Thr Ile Glu Thr
            435                 440                 445

Thr Thr Leu Pro Gln Asp Ala Val Ser Arg Thr Gln Arg Arg Gly Arg
        450                 455                 460

Thr Gly Arg Gly Lys Pro Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Thr Val Arg
                500                 505                 510

Leu Arg Ala Tyr Met Asn Thr Pro Gly Leu Pro Val Cys Gln Asp His
            515                 520                 525

Leu Glu Phe Trp Glu Gly Val Phe Thr Gly Leu Thr His Ile Asp Ala
        530                 535                 540

His Phe Leu Ser Gln Thr Lys Gln Ser Gly Glu Asn Leu Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
                580                 585                 590

His Gly Pro Thr Pro Leu Leu Tyr Arg Leu Gly Ala Val Gln Asn Glu
            595                 600                 605

Ile Thr Leu Thr His Pro Ile Thr Lys Tyr Ile Met Thr Cys Met Ser
        610                 615                 620

Ala Asp Leu Glu Val Val Thr
625                 630

<210> SEQ ID NO 23
<211> LENGTH: 218
<212> TYPE: PRT
<213> ORGANISM: Hepatitis C virus

<400> SEQUENCE: 23

Glu Val Tyr Gln Cys Cys Asp Leu Glu Pro Glu Ala Arg Lys Val Ile
1               5                   10                  15

Ser Ala Leu Thr Glu Arg Leu Tyr Val Gly Gly Pro Met Tyr Asn Ser
            20                  25                  30

Arg Gly Asp Leu Cys Gly Thr Arg Arg Cys Arg Ala Ser Gly Val Phe
        35                  40                  45

Thr Thr Ser Phe Gly Asn Thr Leu Thr Cys Tyr Leu Lys Ala Ser Ala
    50                  55                  60
```

-continued

```
Ala Ile Arg Ala Ala Gly Leu Lys Asp Cys Thr Met Leu Val Cys Gly
 65                  70                  75                  80

Asp Asp Leu Val Val Ile Ala Glu Ser Asp Gly Val Glu Glu Asp Lys
                 85                  90                  95

Arg Ala Leu Gly Ala Phe Thr Glu Ala Met Thr Arg Tyr Ser Ala Pro
            100                 105                 110

Pro Gly Asp Ala Pro Gln Pro Ala Tyr Asp Leu Glu Leu Ile Thr Ser
        115                 120                 125

Cys Ser Ser Asn Val Ser Val Ala His Asp Gly Thr Gly Lys Arg Val
    130                 135                 140

Tyr Tyr Leu Thr Arg Asp Pro Thr Pro Leu Ala Arg Ala Ala Trp
145                 150                 155                 160

Glu Thr Ala Arg His Thr Pro Val Asn Ser Trp Leu Gly Asn Ile Ile
                165                 170                 175

Ile Tyr Ala Pro Thr Ile Trp Val Arg Met Val Leu Met Thr His Phe
            180                 185                 190

Phe Ser Ile Leu Gln Ser Gln Glu Ala Leu Glu Lys Ala Leu Asp Phe
        195                 200                 205

Asp Met Tyr Gly Val Thr Tyr Ser Ile Thr
    210                 215
```

<210> SEQ ID NO 24
<211> LENGTH: 188
<212> TYPE: PRT
<213> ORGANISM: Hepatitis C virus

<400> SEQUENCE: 24

```
Tyr Gln Val Arg Asn Ser Ser Gly Leu Tyr His Val Thr Asn Asp Cys
  1               5                  10                  15

Pro Asn Ser Ser Ile Val Tyr Glu Thr Ala Asp Ile Leu His Ser Pro
                 20                  25                  30

Gly Cys Val Pro Cys Val Arg Glu Gly Asn Thr Ser Lys Cys Trp Val
             35                  40                  45

Ala Val Ala Pro Thr Val Ala Thr Lys Asp Gly Lys Leu Pro Thr Thr
 50                  55                  60

Gln Leu Arg His Ile Asp Leu Leu Val Gly Ala Thr Leu Cys Ser Ala
 65                  70                  75                  80

Leu Tyr Val Gly Asp Leu Cys Gly Ser Val Phe Leu Val Ser Gln Leu
                 85                  90                  95

Phe Thr Phe Ser Pro Arg His Trp Thr Thr Gln Asp Cys Asn Cys Ser
            100                 105                 110

Ile Tyr Pro Gly His Val Thr Gly His Arg Met Ala Trp Asp Met Met
        115                 120                 125

Met Asn Trp Ser Pro Thr Thr Ala Leu Val Val Ala Gln Leu Leu Arg
    130                 135                 140

Val Pro Gln Ala Ile Leu Asp Met Ile Ala Gly Ala His Trp Gly Val
145                 150                 155                 160

Leu Ala Gly Ile Ala Tyr Phe Ser Met Val Gly Asn Trp Ala Lys Val
                165                 170                 175

Leu Val Val Leu Leu Leu Phe Ala Gly Val Asp Ala
            180                 185
```

<210> SEQ ID NO 25
<211> LENGTH: 73
<212> TYPE: PRT
<213> ORGANISM: Hepatitis C virus

```
<400> SEQUENCE: 25

His Trp Gly Val Met Phe Gly Leu Ala Tyr Phe Ser Met Gln Gly Ala
1               5                   10                  15

Trp Ala Lys Val Ile Val Ile Leu Leu Leu Thr Ala Gly Val Asp Ala
            20                  25                  30

Ser Ser His Asn Thr Arg Thr Val Gly Gly Gln Ile Ala Arg Gln Leu
        35                  40                  45

Gln Pro Phe Thr Arg Leu Phe Ser Val Gly Pro Asn Gln Asn Ile Gln
    50                  55                  60

Leu Ile Asn Thr Asn Gly Ser Trp His
65                  70

<210> SEQ ID NO 26
<211> LENGTH: 57
<212> TYPE: PRT
<213> ORGANISM: Hepatitis B virus

<400> SEQUENCE: 26

Ser Thr Thr Ser Thr Gly Pro Cys Arg Thr Cys Met Thr Thr Ala Gln
1               5                   10                  15

Gly Thr Ser Met Tyr Pro Ser Cys Cys Cys Thr Lys Pro Ser Asp Gly
            20                  25                  30

Asn Cys Thr Cys Ile Pro Ile Pro Ser Ser Trp Ala Phe Gly Lys Phe
        35                  40                  45

Leu Trp Glu Trp Ala Ser Ala Arg Phe
    50                  55

<210> SEQ ID NO 27
<211> LENGTH: 88
<212> TYPE: PRT
<213> ORGANISM: Hepatitis B virus

<400> SEQUENCE: 27

Met Gly Gln Asn Leu Ser Val Ser Asn Pro Leu Gly Phe Phe Pro Glu
1               5                   10                  15

His Gln Leu Asp Pro Leu Phe Lys Ala Asn Ser Asn Asn Pro Asp Trp
            20                  25                  30

Asp Phe Asn Pro Asn Lys Asp Asn Trp Pro Glu Ala Thr Gln Val Gly
        35                  40                  45

Val Gly Ala Phe Gly Pro Gly Phe Thr Pro Pro His Gly Gly Leu Leu
    50                  55                  60

Gly Trp Ser Ser Gln Ala Gln Gly Ala Ile Thr Thr Leu Pro Ala Val
65                  70                  75                  80

Pro Pro Ser Ala Ala Thr Asn Arg
                85

<210> SEQ ID NO 28
<211> LENGTH: 220
<212> TYPE: PRT
<213> ORGANISM: Hepatitis B virus

<400> SEQUENCE: 28

Ile Ser Ser Ile Phe Ser Arg Ile Gly Asp Pro Ala Leu Asn Met Glu
1               5                   10                  15

Asn Ile Thr Ser Gly Phe Leu Gly Pro Leu Leu Val Leu Gln Ala Gly
            20                  25                  30

Phe Phe Leu Leu Thr Arg Ile Leu Thr Ile Pro Gln Ser Leu Asp Ser
        35                  40                  45
```

Trp Trp Thr Ser Leu Asn Phe Leu Gly Gly Thr Thr Val Cys Leu Gly
             50                  55                  60

Gln Asn Ser Gln Ser Pro Thr Ser Asn His Ser Pro Thr Ser Cys Pro
 65                  70                  75                  80

Pro Thr Cys Pro Gly Tyr Arg Trp Met Cys Leu Arg Arg Phe Ile Ile
                     85                  90                  95

Phe Leu Phe Ile Leu Leu Leu Cys Leu Ile Phe Leu Leu Val Leu Leu
                100                 105                 110

Asp Tyr Gln Gly Met Leu Pro Val Cys Pro Leu Ile Pro Gly Ser Ser
                115                 120                 125

Thr Thr Ser Thr Gly Pro Cys Arg Thr Cys Thr Thr Pro Ala Gln Gly
            130                 135                 140

Thr Ser Met Tyr Pro Ser Cys Cys Cys Thr Lys Pro Ser Asp Gly Asn
145                 150                 155                 160

Cys Thr Cys Ile Pro Ile Pro Ser Ser Trp Ala Phe Gly Lys Phe Leu
                165                 170                 175

Trp Glu Trp Ala Ser Ala Arg Phe Ser Trp Leu Ser Leu Leu Val Pro
                180                 185                 190

Phe Val Gln Trp Phe Val Gly Leu Ser Pro Thr Val Trp Leu Ser Val
                195                 200                 205

Ile Trp Met Met Trp Tyr Trp Gly Pro Ser Leu Tyr
                210                 215                 220

<210> SEQ ID NO 29
<211> LENGTH: 175
<212> TYPE: PRT
<213> ORGANISM: Human cytomegalovirus

<400> SEQUENCE: 29

Tyr Asn Lys Pro Ile Ala Ala Arg Phe Met Gly Asp Val Leu Gly Leu
 1               5                  10                  15

Ala Ser Cys Val Thr Ile Asn Gln Thr Ser Val Lys Val Leu Arg Asp
                20                  25                  30

Met Asn Val Lys Glu Ser Pro Gly Arg Cys Tyr Ser Arg Pro Val Val
             35                  40                  45

Ile Phe Asn Phe Val Asn Ser Ser Tyr Val Gln Tyr Gly Gln Leu Gly
 50                  55                  60

Glu Asp Asn Glu Ile Leu Gly Asn His Arg Thr Glu Glu Cys Gln
 65                  70                  75                  80

Phe Pro Ser Leu Lys Ile Phe Ile Ala Gly Asn Ser Ala Tyr Glu Tyr
                 85                  90                  95

Val Asp Tyr Leu Phe Lys Arg Met Ile Asp Leu Ser Ser Ile Tyr Thr
                100                 105                 110

Val Asp Ser Met Ile Ala Leu Asp Ile Asp Pro Leu Glu Asn Thr Asp
            115                 120                 125

Phe Arg Val Leu Glu Leu Tyr Ser Gln Lys Glu Leu Arg Ser Ser Asn
            130                 135                 140

Val Phe Asp Leu Glu Glu Ile Met Arg Glu Phe Asn Ser Tyr Lys Gln
145                 150                 155                 160

Arg Val Lys Tyr Val Glu Asp Lys Val Val Asp Pro Leu Pro Pro
                165                 170                 175

<210> SEQ ID NO 30
<211> LENGTH: 551
<212> TYPE: PRT
<213> ORGANISM: Human cytomegalovirus

<400> SEQUENCE: 30

```
Met Ala Ser Val Leu Gly Pro Ile Ser Gly His Val Leu Lys Ala Val
1               5                   10                  15
Phe Ser Arg Gly Asp Thr Pro Val Leu Pro His Glu Thr Arg Leu Leu
            20                  25                  30
Gln Thr Gly Ile His Val Arg Val Ser Gln Pro Ser Leu Ile Leu Val
        35                  40                  45
Ser Gln Tyr Thr Pro Asp Ser Thr Pro Cys His Arg Gly Asp Asn Gln
    50                  55                  60
Leu Gln Val Gln His Thr Tyr Phe Thr Gly Ser Glu Val Glu Asn Val
65                  70                  75                  80
Ser Val Asn Val His Asn Pro Thr Gly Arg Ser Ile Cys Pro Ser Gln
                85                  90                  95
Glu Pro Met Ser Ile Tyr Val Tyr Ala Leu Pro Leu Lys Met Leu Asn
            100                 105                 110
Ile Pro Ser Ile Asn Val His Tyr Pro Ser Ala Ala Glu Arg Lys
        115                 120                 125
His Arg His Leu Pro Val Ala Asp Ala Val Ile His Ala Ser Gly Lys
    130                 135                 140
Gln Met Trp Gln Ala Arg Leu Thr Val Ser Gly Leu Ala Trp Thr Arg
145                 150                 155                 160
Gln Gln Asn Gln Trp Lys Glu Pro Asp Val Tyr Tyr Thr Ser Ala Phe
                165                 170                 175
Val Phe Pro Thr Lys Asp Val Ala Leu Arg His Val Val Cys Ala His
            180                 185                 190
Glu Leu Val Cys Ser Met Glu Asn Thr Arg Ala Thr Lys Met Gln Val
        195                 200                 205
Ile Gly Asp Gln Tyr Val Lys Val Tyr Leu Glu Ser Phe Cys Glu Asp
    210                 215                 220
Val Pro Ser Gly Lys Leu Phe Met His Val Thr Leu Gly Ser Asp Val
225                 230                 235                 240
Glu Glu Asp Leu Thr Met Thr Arg Asn Pro Gln Pro Phe Met Arg Pro
                245                 250                 255
His Glu Arg Asn Gly Phe Thr Val Leu Cys Pro Lys Asn Met Ile Ile
            260                 265                 270
Lys Pro Gly Lys Ile Ser His Ile Met Leu Asp Val Ala Phe Thr Ser
        275                 280                 285
His Glu His Phe Gly Leu Leu Cys Pro Lys Ser Ile Pro Gly Leu Ser
    290                 295                 300
Ile Ser Gly Asn Leu Leu Met Asn Gly Gln Gln Ile Phe Leu Glu Val
305                 310                 315                 320
Gln Ala Ile Arg Glu Thr Val Glu Leu Arg Gln Tyr Asp Pro Val Ala
                325                 330                 335
Ala Leu Phe Phe Phe Asp Ile Asp Leu Leu Leu Gln Arg Gly Pro Gln
            340                 345                 350
Tyr Ser Glu His Pro Thr Phe Thr Ser Gln Tyr Arg Ile Gln Gly Lys
        355                 360                 365
Leu Glu Tyr Arg His Thr Trp Asp Arg His Asp Glu Gly Ala Ala Gln
    370                 375                 380
Gly Asp Asp Asp Val Trp Thr Ser Gly Ser Ser Asp Glu Glu Leu
385                 390                 395                 400
Val Thr Thr Glu Arg Lys Thr Pro Arg Val Thr Gly Gly Gly Ala Met
                405                 410                 415
```

Ala Gly Ala Ser Thr Ser Ala Gly Arg Lys Arg Lys Ser Ala Ser Ser
                420                 425                 430

Ala Thr Ala Cys Thr Ala Gly Val Met Thr Arg Gly Arg Leu Lys Ala
                435                 440                 445

Glu Ser Thr Val Ala Pro Glu Glu Asp Thr Asp Glu Asp Ser Asp Asn
            450                 455                 460

Glu Ile His Asn Pro Ala Val Phe Thr Trp Pro Trp Gln Ala Gly
465                 470                 475                 480

Ile Leu Ala Arg Asn Leu Val Pro Met Val Ala Thr Val Gln Gly Gln
                485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
            515                 520                 525

Arg Arg Arg His Arg Gln Asp Ala Leu Pro Gly Pro Cys Ile Ala Ser
            530                 535                 540

Thr Pro Lys Lys His Arg Gly
545                 550

<210> SEQ ID NO 31
<211> LENGTH: 491
<212> TYPE: PRT
<213> ORGANISM: Human cytomegalovirus

<400> SEQUENCE: 31

Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
                20                  25                  30

Thr Thr Phe Leu Gln Thr Met Leu Arg Lys Glu Val Asn Ser Gln Leu
            35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Val Lys Gln Ile Lys Val Arg Val Asp Met Val
                85                  90                  95

Arg His Arg Ile Lys Glu His Met Leu Lys Lys Tyr Ala Gln Thr Glu
                100                 105                 110

Glu Lys Phe Thr Gly Ala Phe Asn Met Met Gly Gly Cys Leu Gln Asn
            115                 120                 125

Ala Leu Asp Ile Leu Asp Lys Val His Glu Pro Phe Glu Glu Met Lys
130                 135                 140

Cys Ile Gly Leu Thr Met Gln Ser Met Tyr Glu Asn Tyr Ile Val Pro
145                 150                 155                 160

Glu Asp Lys Arg Glu Met Trp Met Ala Cys Ile Lys Glu Leu His Asp
                165                 170                 175

Val Ser Lys Gly Ala Ala Asn Lys Leu Gly Gly Ala Leu Lys Ala Lys
            180                 185                 190

Ala Arg Ala Lys Lys Asp Glu Leu Arg Arg Lys Met Met Tyr Met Cys
        195                 200                 205

Tyr Arg Asn Ile Glu Phe Phe Thr Lys Asn Ser Ala Phe Pro Lys Thr
    210                 215                 220

Thr Asn Gly Cys Ser Gln Ala Met Ala Ala Leu Gln Asn Leu Pro Gln
225                 230                 235                 240

```
Cys Ser Pro Asp Glu Ile Met Ser Tyr Ala Gln Lys Ile Phe Lys Ile
                245                 250                 255

Leu Asp Glu Glu Arg Asp Lys Val Leu Thr His Ile Asp His Ile Phe
            260                 265                 270

Met Asp Ile Leu Thr Thr Cys Val Glu Thr Met Cys Asn Glu Tyr Lys
        275                 280                 285

Val Thr Ser Asp Ala Cys Met Met Thr Met Tyr Gly Gly Ile Ser Leu
    290                 295                 300

Leu Ser Glu Phe Cys Arg Val Leu Cys Cys Tyr Val Leu Glu Glu Thr
305                 310                 315                 320

Ser Val Met Leu Ala Lys Arg Pro Leu Ile Thr Lys Pro Glu Val Ile
                325                 330                 335

Ser Val Met Lys Arg Arg Ile Glu Glu Ile Cys Met Lys Val Phe Ala
                340                 345                 350

Gln Tyr Ile Leu Gly Ala Asp Pro Leu Arg Val Cys Ser Pro Ser Val
            355                 360                 365

Asp Asp Leu Arg Ala Ile Ala Glu Ser Asp Glu Asp Ala Ile
        370                 375                 380

Ala Ala Tyr Thr Leu Ala Thr Ala Gly Ala Ser Ser Asp Ser Leu
385                 390                 395                 400

Val Ser Pro Glu Ser Pro Val Pro Ala Thr Ile Pro Leu Ser Ser
                405                 410                 415

Val Ile Val Ala Glu Asn Ser Asp Gln Glu Glu Ser Glu Gln Ser Asp
                420                 425                 430

Glu Glu Gln Glu Glu Gly Ala Gln Glu Glu Arg Glu Asp Thr Val Ser
            435                 440                 445

Val Lys Ser Glu Pro Val Ser Glu Ile Glu Glu Val Ala Ser Glu Lys
        450                 455                 460

Glu Glu Asp Gly Ala Glu Glu Pro Thr Thr Ser Gly Gly Lys Ser Thr
465                 470                 475                 480

His Pro Met Val Thr Arg Ser Lys Ala Asp Gln
                485                 490

<210> SEQ ID NO 32
<211> LENGTH: 100
<212> TYPE: PRT
<213> ORGANISM: Human cytomegalovirus

<400> SEQUENCE: 32

Met Lys Pro Val Leu Val Leu Ala Ile Leu Ala Val Leu Phe Leu Arg
1               5                   10                  15

Leu Ala Asp Ser Val Pro Arg Pro Leu Asp Val Val Ser Glu Ile
            20                  25                  30

Arg Ser Ala His Phe Arg Val Glu Glu Asn Gln Cys Trp Phe His Met
        35                  40                  45

Gly Met Leu Tyr Phe Lys Gly Arg Met Ser Gly Asn Phe Thr Glu Lys
    50                  55                  60

His Phe Val Asn Val Gly Ile Val Ser Gln Ser Tyr Met Asp Arg Leu
65                  70                  75                  80

Gln Val Ser Gly Glu Gln Tyr His His Asp Glu Arg Gly Ala Tyr Phe
                85                  90                  95

Glu Trp Asn Ile
            100
```

```
<210> SEQ ID NO 33
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 33

Arg Ala His Tyr Ser Ile Val Thr Phe
1               5
```

LIPIDATED TUMOR-ASSOCIATED ANTIGENS AND IMMUNOTHERAPEUTIC COMPOSITIONS

RELATED APPLICATION

This application claims priority of U.S. Provisional Application No. 61/219,301, filed on Jun. 22, 2009. The prior application is incorporated herein by reference in its entirety.

BACKGROUND

Viral infection causes various disorders, including cancer. For example, human papillomaviruses (HPVs) infection accounts for the development of several cancers, in particular the cervical cancer, the second leading cause of cancer death in women worldwide (Schwarz, *Expert Rev Vaccines* 7:1465-73, 2008). It was estimated that about 493,000 new cervical cancer cases were diagnosed per year (Parkin et al., *CA Cancer J Clin* 55:74-108, 2005). Vaccines are being developed for preventing infections with cancer-causing viruses, treating existing cancer, or preventing the development of cancer in high risk individuals. However, many are not effective. There is a need for effective vaccines and related reagents.

SUMMARY

This invention relates to novel polypeptides, fusion proteins, immunotherapeutic compositions, and methods.

Accordingly, one aspect of the invention features an isolated polypeptide having the sequence of SEQ ID NO.: 2 (shown in FIG. 1B). Also featured is an isolated nucleic acid having a sequence encoding the polypeptide or its complement. Example of the nucleic acid including SEQ ID NO: 13 (shown below) and its degenerate variants where one or more codons are replaced by other codons encoding the same residues.

```
                                    (SEQ ID NO.: 13)
ATGCATGGCGATACCCCGACCCTGCATGAATATATGCTGGATCTGCAG

CCGGAAACCACCGATCTGTATGGCTATCAGCAGCTGAACGATAGCAGC

GAAGAAGAAGATGAAATTGATGGCCCGGCGGGCCAGGCGGAACCGGAT

CGCGCGCATTATAACATTGTGACCTTTGCGAGCAAAGCGGATAGCACC

CTGCGCCTGAGCGTGCAGAGCACCCATGTGGATATTCGCACCCTGGAA

GATCTGCTGATGGGCACCCTGGGCATTGTGGCGCCGATTGCGAGCCAG

AAACCG
```

The invention also features an isolated fusion protein having a first segment having a lipidating sequence and a second segment having the sequence of a tumor associate antigen. The first segment is located at the N-terminus to the second segment in the fusion protein. In one example, the fusion protein is lipidated. The lipidating sequence includes: Met Lys Lys Leu Leu Ile Ala Ala Met Met Ala Ala Ala Leu Ala Ala Cys Ser Gln Glu Ala Lys Gln Glu Val Lys Glu Ala Val Gln Ala Val Glu Ser Asp Val Lys Asp Thr Ala (SEQ ID NO: 12). The tumor-associated antigen can be a viral antigen derived from a virus associated with a human chronic disease or cancer (such as cervical cancer). In one example, the viral antigen is derived from Epstein-Barr virus (EBV), human papillomavirus (HPV), hepatitis C virus (HCV), hepatitis B virus (HBV), or cytomegalovirus (CMV). In one embodiment, the viral antigen is an inactive HPV oncoproteins E5, E6, or E7. In a preferred embodiment, the viral antigen is an HPV 16 E7 oncoprotein, such as SEQ ID NO: 1 or 2. Examples of the fusion protein include an rlipo-E7m fusion protein described in the working example below. Shown below are the amino acid sequence of the rlipo-E7m fusion protein and a nucleic acid encoding this fusion protein (SEQ ID NOs: 14 and 15):

```
                                              (SEQ ID NO: 14)
Met Lys Lys Leu Leu Ile Ala Ala Met Met Ala Ala

Ala Leu Ala Ala Cys Ser Gln Glu Ala Lys Gln Glu

Val Lys Glu Ala Val Gln Ala Val Glu Ser Asp Val

Lys Asp Thr Ala Gly Ser Met His Gly Asp Thr Pro

Thr Leu His Glu Tyr Met Leu Asp Leu Gln Pro Glu

Thr Thr Asp Leu Tyr Gly Tyr Gln Gln Leu Asn Asp

Ser Ser Glu Glu Glu Asp Glu Ile Asp Gly Pro Ala

Gly Gln Ala Glu Pro Asp Arg Ala His Tyr Asn Ile

Val Thr Phe Ala Ser Lys Ala Asp Ser Thr Leu Arg

Leu Ser Val Gln Ser Thr His Val Asp Ile Arg Thr

Leu Glu Asp Leu Leu Met Gly Thr Leu Gly Ile Val

Ala Pro Ile Ala Ser Gln Lys Pro.
```

```
                                              (SEQ ID NO: 15)
ATGAAAAAACTGCTGATTGCGGCGATGATGGCGGCGGCGCTGGCGGC

GTGCAGCCAGGAAGCGAAACAGGAAGTGAAAGAAGCGGTGCAGGCGG

TGGAAAGCGATGTGAAAGATACCGCGGGATCCATGCATGGCGATACC

CCGACCCTGCATGAATATATGCTGGATCTGCAGCCGGAAACCACCGA

TCTGTATGGCTATCAGCAGCTGAACGATAGCAGCGAAGAAGAAGATG

AAATTGATGGCCCGGCGGGCCAGGCGGAACCGGATCGTGCGCATTAT

AACATTGTGACCTTTGCGAGCAAAGCGGATAGCACCCTGCGTCTGAG

CGTGCAGAGCACCCATGTGGATATTCGTACCCTGGAAGATCTGCTGA

TGGGCACCCTGGGCATTGTGGCGCCGATTGCGAGCCAGAAACCG.
```

The invention also features an isolated nucleic acid that contains a sequence encoding the just-described fusion protein or the complement of the nucleic acid. Example of the nucleic acid including SEQ ID NO: 15 and its degenerate variants where one or more codons are replaced by other codons encoding the same residues.

A nucleic acid refers to a DNA molecule (e.g., a cDNA or genomic DNA), an RNA molecule (e.g. an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide or protein of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A regulatory sequence includes promoters, enhancers, and other expression control elements (e.g., T7 promoter, cauliflower mosaic virus 35S promoter sequences or polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide or fusion protein of this invention.

Also within the scope of this invention is a host cell that contains the above-described nucleic acid. Examples include E. coli cells, insect cells (e.g., using baculovirus expression vectors), plant cells, yeast cells, or mammalian cells. See e.g., Goeddel, (1990) Gene Expression Technology: Methods in Enzymology 185, Academic Press, San Diego, Calif.

To produce a fusion protein/polypeptide of this invention, one can culture a host cell in a medium under conditions permitting expression of the fusion protein/polypeptide encoded by a nucleic acid of this invention, and purify the fusion protein/polypeptide from the cultured cell or the medium. Alternatively, the nucleic acid of this invention can be transcribed and translated in vitro, for example, using T7 promoter regulatory sequences and T7 polymerase in cell lysate from, e.g., E. coli. The lipidated fusion protein can include, from N-terminus to C-terminus, D1 fragment of Ag473 and a target protein, such as an antigenic viral protein.

In another aspect, the invention features an immunogenic composition comprising the above-described polypeptide or fusion protein. The immunogenic composition can be formulated or not formulated with a pharmaceutically acceptable adjuvant.

In yet another aspect, the invention features a method of inducing an immune response to a virus, such HPV. The method includes the step of administering to a subject in need thereof an effective amount of the above-described immunogenic composition. A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, etc. In a preferred embodiment, the subject is a human. In another embodiment, the subject is an experimental animal or animal suitable as a disease model.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B are the amino acid sequences of wild-type HPV16 E7 protein (1A; SEQ ID NO: 1) and inactive E7 protein, E7m (1B; SEQ ID NO: 2).

FIGS. 2A and 2B are photographs showing recombinant E7m (rE7m; 2A) and recombinant lipoproteinrlipo-E7m (rlipo-E7m; 2B) purified by IMAC and monitored by 15% SDS-PAGE under reducing conditions and with Coomassie Blue staining (left panels) or immunoblot monitoring using anti-(His)6 antibodies (right panels). (A) Lane 1: cell lysate after IPTG induction; lane 2: cell lysate before IPTG induction; lane 3: soluble fraction of induced cells; lane 4: purified rE7m; lanes 5-8: immunoblots; (B) Lane 1: cell lysate after IPTG induction; lane 2: cell lysate before IPTG induction; lane 3: purified rlipo-E7m; lanes 4-6: immunoblots.

FIGS. 3A and 3B are diagrams showing identification of intact and N-terminal fragments of rlipo-E7m protein.

DETAILED DESCRIPTION

Figure 4:
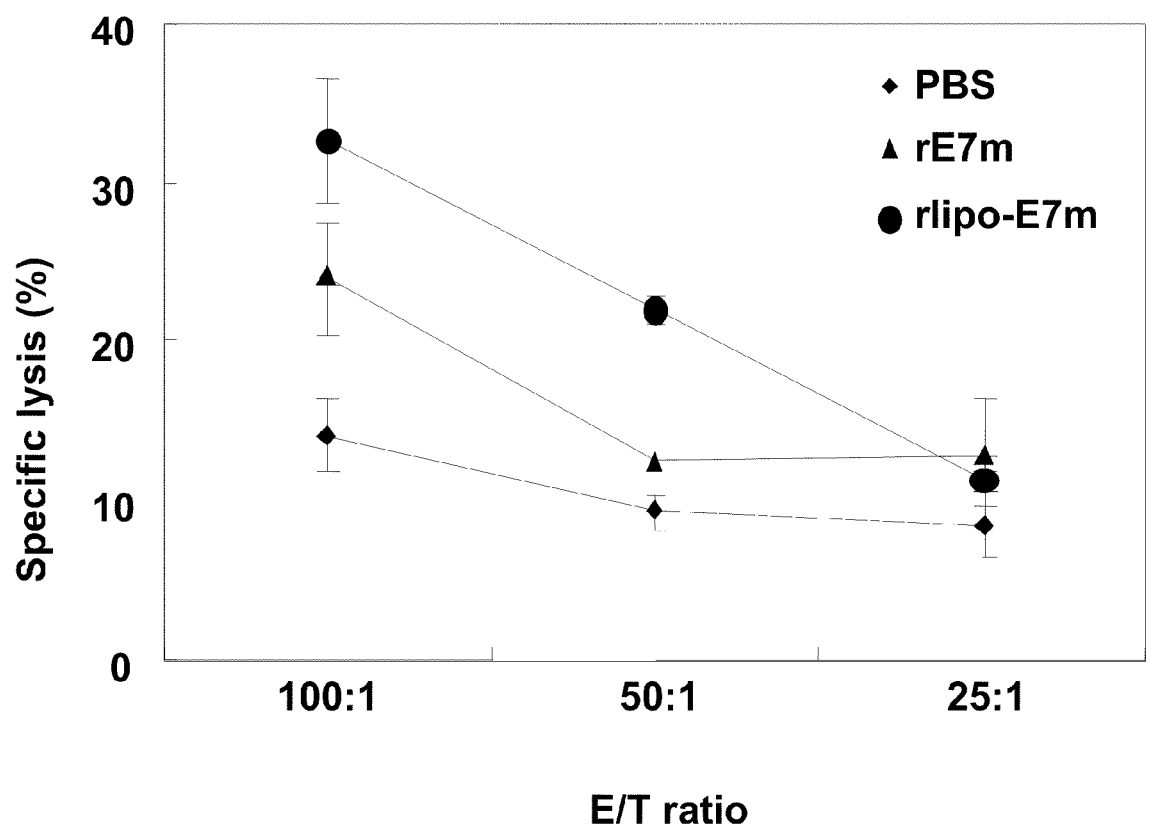
FIG. 4 is a diagram showing induction of tumor-specific cytotoxic T lymphocytes (CTL) responses by rlipo-E7m in C57BL/6 mice.

This invention is based, at least in part, on the unexpected discoveries of a novel mutant of a tumor-associate antigen, and a fusion protein of a tumor-associate antigen and a lipidating sequence. The fusion protein, unexpectedly, can be lipidated and expressed at a high amount in bacterial cells, such as E. coli. cells. Once administered to a subject, both induced immune responses (e.g., cytotoxic T lymphocytes or antibodies) against a tumor.

The invention features an immunogenic composition, such as a vaccine, against virus infection and/or related other disorders, e.g., cancer. As mentioned above, the immunogenic composition can contain a recombinant fusion protein. The fusion protein has a first segment having a lipidating sequence and a second segment having the sequence of a tumor associated antigen.

The tumor-associated antigen can be a viral antigen derived from a virus associated with a human chronic disease or cancer (such as cervical cancer). In one example, the viral antigen is derived from Epstein-Barr virus (EBV), HPV, hepatitis C virus (HCV), hepatitis B virus (HBV), or cytomegalovirus (CMV). Shown below are sequences of exemplary viral antigens. There proteins and their antigenic fragments can be used to make immunogenic compositions of this invention.

Human Herpesvirus 4 (Epstein-Barr Virus), Latent Membrane Protein-1 (LMP1):

```
                                          (SEQ ID NO: 16)
MetGluArgAspLeuGluArgGlyProProGlyProProArgProPro

LeuGlyProProLeuSerSerSerIleGlyLeuAlaLeuLeuLeuLeu

LeuLeuAlaLeuLeuPheTrpLeuTyrIleValMetSerAspTrpThr

GlyGlyAlaLeuLeuValLeuTyrSerPheAlaLeuMetLeuIleIle

IleIleLeuIleIlePheIlePheArgArgAspLeuLeuCysProLeu

GlyGlyLeuGlyLeuLeuLeuLeuMetIleThrLeuLeuLeuIleAla

LeuTrpAsnLeuHisGlyGlnAlaLeuTyrLeuGlyIleValLeuPhe
```

-continued
IlePheGlyCysLeuLeuValLeuGlyLeuTrpIleTyrPheLeuGlu
IleLeuTrpArgLeuGlyAlaThrLeuTrpGlnLeuLeuAlaPheIle
LeuAlaPhePheLeuAlaIleIleLeuLeuIleIleAlaLeuTyrLeu
GlnGlnAsnTrpTrpThrLeuLeuValAspLeuLeuTrpLeuLeuLeu
PheMetAlaIleLeuIleTrpMetTyrTyrHisGlyProArgHisThr
AspGluHisHisHisAspAspSerLeuProHisProGlnGlnAlaThr
AspAspSerSerHisGluSerAspSerAsnSerAsnGluGlyArgHis
HisLeuLeuValSerGlyAlaGlyAspGlyProProLeuCysSerGln
AsnLeuGlyAlaProGlyGlyGlyProAspAsnGlyProGlnAspPro
AspAsnThrAspAspAsnGlyProGlnAspProAspAsnThrAspAsp
AsnGlyProGlnAspProAspAsnThrAspAspAsnGlyProGlnAsp
ProAspAsnThrAspAspAsnGlyProGlnAspProAspAsnThrAsp
AspAsnGlyProGlnAspProAspAsnThrAspAspAsnGlyProGln
AspProAspAsnThrAspAspAsnGlyProHisAspProLeuProHis
AsnProSerAspSerAlaGlyAsnAspGlyGlyProProAsnLeuThr
GluGluValAlaAsnLysGlyGlyAspArgGlyProProSerMetThr
AspGlyGlyGlyGlyAspProHisLeuProThrLeuLeuLeuGlyThr
SerGlySerGlyGlyAspAspAspAspProHisGlyProValGlnLeu
SerTyrTyrAsp Human Herpesvirus 4 (Epstein-Barr Virus), Terminal Protein LMP-2A:

(SEQ ID NO: 17)
MetGlySerLeuGluMetValProMetGlyAlaGlyProProSerPro
GlyGlyAspProAspGlyAspAspGlyGlyAsnAsnSerGlnTyrPro
SerAlaSerGlySerSerGlyAsnThrProThrProProAsnAspGlu
GluArgGluSerAsnGluGluProProProProTyrGluAspProTyr
TrpGlyAsnGlyAspArgHisSerAspTyrGlnProLeuGlyThrGln
AspGlnSerLeuTyrLeuGlyLeuGlnHisAspGlyAsnAspGlyLeu
ProProProProTyrSerProArgAspAspSerSerGlnHisIleTyr
GluGluAlaGlyArgGlySerMetAsnProValCysLeuProValIle
ValAlaProTyrLeuPheTrpLeuAlaAlaIleAlaAlaSerCysPhe
ThrAlaSerValSerThrValValThrAlaThrGlyLeuAlaLeuSer
LeuLeuLeuLeuAlaAlaValAlaSerSerTyrAlaAlaAlaGlnArg
LysLeuLeuThrProValThrValLeuThrAlaValValThrPhePhe
AlaIleCysLeuThrTrpArgIleGluAspProProPheAsnSerLeu
LeuPheAlaLeuLeuAlaAlaAlaGlyGlyLeuGlnGlyIleTyrVal
LeuValMetLeuValLeuLeuIleLeuAlaTyrArgArgArgTrpArg
ArgLeuThrValCysGlyGlyIleMetPheLeuAlaCysValLeuVal
LeuIleValAspAlaValLeuGlnLeuSerProLeuLeuGlyAlaVal
ThrValValSerMetThrLeuLeuLeuLeuAlaPheValLeuTrpLeu
SerSerProGlyGlyLeuGlyThrLeuGlyAlaAlaLeuLeuThrLeu

-continued
AlaAlaAlaLeuAlaLeuLeuAlaSerLeuIleLeuGlyThrLeuAsn
LeuThrThrMetPheLeuLeuMetLeuLeuTrpThrLeuValValLeu
LeuIleCysSerSerCysSerSerCysProLeuSerLysIleLeuLeu
AlaArgLeuPheLeuTyrAlaLeuAlaLeuLeuLeuLeuAlaSerAla
LeuIleAlaGlyGlySerIleLeuGlnThrAsnPheLysSerLeuSer
SerThrGluPheIleProAsnLeuPheCysMetLeuLeuLeuIleVal
AlaGlyIleLeuPheIleLeuAlaIleLeuThrGluTrpGlySerGly
AsnArgThrTyrGlyProValPheMetCysLeuGlyGlyLeuLeuThr
MetValAlaGlyAlaValTrpLeuThrValMetThrAsnThrLeuLeu
SerAlaTrpIleLeuThrAlaGlyPheLeuIlePheLeuIleGlyPhe
AlaLeuPheGlyValIleArgCysCysArgTyrCysCysTyrTyrCys
LeuThrLeuGluSerGluGluArgProProThrProTyrArgAsnThr
Val Human Herpesvirus 4 (Epstein-Barr Virus), Terminal Protein LMP-2B (SEQ ID NO: 18)
MetAsnProValCysLeuProValIleValAlaProTyrLeuPheTrp
LeuAlaAlaIleAlaAlaSerCysPheThrAlaSerValSerThrVal
ValThrAlaThrGlyLeuAlaLeuSerLeuLeuLeuLeuAlaAlaVal
AlaSerSerTyrAlaAlaAlaGlnArgLysLeuLeuThrProValThr
ValLeuThrAlaValValThrPhePheAlaIleCysLeuThrTrpArg
IleGluAspProProPheAsnSerLeuLeuPheAlaLeuLeuAlaAla
AlaGlyGlyLeuGlnGlyIleTyrValLeuValMetLeuValLeuLeu
IleLeuAlaTyrArgArgArgTrpArgArgLeuThrValCysGlyGly
IleMetPheLeuAlaCysValLeuValLeuIleValAspAlaValLeu
GlnLeuSerProLeuLeuGlyAlaValThrValValSerMetThrLeu
LeuLeuLeuAlaPheValLeuTrpLeuSerSerProGlyGlyLeuGly
ThrLeuGlyAlaAlaLeuLeuThrLeuAlaAlaAlaLeuAlaLeuLeu
AlaSerLeuIleLeuGlyThrLeuAsnLeuThrThrMetPheLeuLeu
MetLeuLeuTrpThrLeuValValLeuLeuIleCysSerSerCysSer
SerCysProLeuSerLysIleLeuLeuAlaArgLeuPheLeuTyrAla
LeuAlaLeuLeuLeuLeuAlaSerAlaLeuIleAlaGlyGlySerIle
LeuGlnThrAsnPheLysSerLeuSerSerThrGluPheIleProAsn
LeuPheCysMetLeuLeuLeuIleValAlaGlyIleLeuPheIleLeu
AlaIleLeuThrGluTrpGlySerGlyAsnArgThrTyrGlyProVal
PheMetCysLeuGlyGlyLeuLeuThrMetValAlaGlyAlaValTrp
LeuThrValMetSerAsnThrLeuLeuSerAlaTrpIleLeuThrAla
GlyPheLeuIlePheLeuIleGlyPheAlaLeuPheGlyValIleArg
CysCysArgTyrCysCysTyrTyrCysLeuThrLeuGluSerGluGlu
ArgProProThrProTyrArgAsnThrVal Human Herpesvirus 4 (Epstein-Barr Virus), Envelope Glycoprotein gp350

(SEQ ID NO: 19)
MetGluAlaAlaLeuLeuValCysGlnTyrThrIleGlnSerLeuIle
GlnLeuThrArgAspAspProGlyPhePheAsnValGluIleLeuGlu
PheProPheTyrProAlaCysAsnValCysThrAlaAspValAsnAla
ThrIleAsnPheAspValGlyGlyLysLysHisLysLeuAsnLeuAsp
PheGlyLeuLeuThrProHisThrLysAlaValTyrGlnProArgGly
AlaPheGlyGlySerGluAsnAlaThrAsnLeuPheLeuLeuGluLeu
LeuGlyAlaGlyGluLeuAlaLeuThrMetArgSerLysLysLeuPro
IleAsnIleThrThrGlyGluGluGlnGlnValSerLeuGluSerVal
AspValTyrPheGlnAspValPheGlyThrMetTrpCysHisHisAla
GluMetGlnAsnProValTyrLeuIleProGluThrValProTyrIle
LysTrpAspAsnCysAsnSerThrAsnIleThrAlaValValArgAla
GlnGlyLeuAspValThrLeuProLeuSerLeuProThrSerAlaGln
AspSerAsnPheSerValLysThrGluMetLeuGlyAsnGluIleAsp
IleGluCysIleMetGluAspGlyGluIleSerGlnValLeuProGly
AspAsnLysPheAsnIleThrCysSerGlyTyrGluSerHisValPro
SerGlyGlyIleLeuThrSerThrSerProValAlaThrProIlePro
GlyThrGlyTyrAlaTyrSerLeuArgLeuThrProArgProValSer
ArgPheLeuGlyAsnAsnSerIleLeuTyrValPheTyrSerGlyAsn
GlyProLysAlaSerGlyGlyAspTyrCysIleGlnSerAsnIleVal
PheSerAspGluIleProAlaSerGlnAspMetProThrAsnThrThr
AspIleThrTyrValGlyAspAsnAlaThrTyrSerValProMetVal
ThrSerGluAspAlaAsnSerProAsnValThrValThrAlaPheTrp
AlaTrpProAsnAsnThrGluThrAspPheLysCysLysTrpThrLeu
ThrSerGlyThrProSerGlyCysGluAsnIleSerGlyAlaPheAla
SerAsnArgThrPheAspIleThrValSerGlyLeuGlyThrAlaPro
LysThrLeuIleIleThrArgThrAlaThrAsnAlaThrThrThrThr
HisLysValIlePheSerLysAlaProGluSerThrThrThrSerPro
ThrLeuAsnThrThrGlyPheAlaAlaProAsnThrThrThrGlyLeu
ProSerSerThrHisValProThrAsnLeuThrAlaProAlaSerThr
GlyProThrValSerThrAlaAspValThrSerProThrProAlaGly
ThrThrSerGlyAlaSerProValThrProSerProSerProArgAsp
AsnGlyThrGluSerLysAlaProAspMetThrSerProThrSerAla
ValThrThrProThrProAsnAlaThrSerProThrProAlaValThr
ThrProThrProAsnAlaThrSerProThrLeuGlyLysThrSerPro
ThrSerAlaValThrThrProThrProAsnAlaThrSerProThrPro
AlaValThrThrProThrProAsnAlaThrIleProThrLeuGlyLys
ThrSerProThrSerAlaValThrThrProThrProAsnAlaThrSer
ProThrValGlyGluThrSerProGlnAlaAsnThrThrAsnHisThr
LeuGlyGlyThrSerSerThrProValValThrSerProProLysAsn
AlaThrSerAlaValThrThrGlyGlnHisAsnIleThrSerSerSer
ThrSerSerMetSerLeuArgProSerSerIleSerGluThrLeuSer
ProSerThrSerAspAsnSerThrSerHisMetProLeuLeuThrSer
AlaHisProThrGlyGlyGluAsnIleThrGlnValThrProAlaSer
ThrSerThrHisHisValSerThrSerSerProAlaProArgProGly
ThrThrSerGlnAlaSerGlyProGlyAsnSerSerThrSerThrLys
ProGlyGluValAsnValThrLysGlyThrProProLysAsnAlaThr
SerProGlnAlaProSerGlyGlnLysThrAlaValProThrValThr
SerThrGlyGlyLysAlaAsnSerThrThrGlyGlyLysHisThrThr
GlyHisGlyAlaArgThrSerThrGluProThrThrAspTyrGlyGly
AspSerThrThrProArgThrArgTyrAsnAlaThrThrTyrLeuPro
ProSerThrSerSerLysLeuArgProArgTrpThrPheThrSerPro
ProValThrThrAlaGlnAlaThrValProValProProThrSerGln
ProArgPheSerAsnLeuSerMetLeuValLeuGlnTrpAlaSerLeu
AlaValLeuThrLeuLeuLeuLeuLeuValMetAlaAspCysAlaPhe
ArgArgAsnLeuSerThrSerHisThrTyrThrThrProProTyrAsp
AspAlaGluThrTyrVal

Human Herpesvirus 4 (Epstein-Barr Virus), EBNA-2 Nuclear Protein (SEQ ID NO: 20)
MetProThrTyrTyrLeuAlaLeuHisGlyGlyGlnSerTyrAsnLeu
IleValAspThrAspMetSerGlyAsnProSerLeuSerValIlePro
ThrAsnProTyrGlnGluGlnLeuSerAsnAsnProLeuIleGlnLeu
GlnIleValValGlyGluAsnThrGlyAlaProAlaProProGlnPro
ProProProProProProProProProGluArgArgAspAlaTrp
ThrGlnGluProLeuProLeuAspMetAsnProLeuGlySerAspAla
SerGlnGlyProLeuAlaSerSerIleArgMetLeuCysMetAlaGln
TyrLeuLeuArgAsnAlaArgGlyGlnGlnGlyLeuLeuArgProLeu
GlyProGlnThrArgSerGlnValThrLeuGluArgGlnProValHis
AsnProArgGlnGluAlaProIleIleLeuLeuGlnSerProAlaPro
ProArgPheThrProValProMetValAlaLeuGlyHisThrLeuGln
ProThrProProArgProThrLeuProGlnProArgIleProLeu
IleIleProProArgHisThrAsnGlnProAlaThrThrProProThr
AlaProGlnArgLeuThrLeuGlyHisGlnLeuSerLeuProProHis
ProProProHisGlnSerThrProHisCysSerSerAspSerThrGly
LeuProProProProThrSerTyrSerIleProSerMetThrLeuSer
ProGluProLeuProProAlaAlaProAlaHisProLeuProGly
ValIleTyrAspGlnGlnAlaLeuProProThrProGlyProProTrp
TrpProProValArgAspProThrProThrThrGlnThrProProThr
AsnThrLysGlnGlyProAspGlnGlyGlnGlyArgGlyArgTrpArg -continued GlyArgGlyArgSerLysGlyArgGlyArgMetHisLysLeuProGlu ProArgArgProGlyProAspThrSerSerProSerMetProGlnLeu SerProValValSerLeuHisGlnGlnGlyProGluAsnSerPro ThrProGlyProSerThrAlaGlyProValCysArgValThrProSer AlaThrProAspIleSerProIleHisGluProGluSerSerAspSer GluGluProProPheLeuPheProSerAspTrpTyrProProThrLeu GluProAlaGluLeuAspGluSerTrpGluGlyIlePheGluThrThr GluSerHisSerSerAspGluGluAsnValGlyGlyProSerLysArg ProArgThrSerThrGln Human Herpesvirus 4 (Epstein-Barr Virus), EBNA-3C Nuclear Protein (SEQ ID NO: 21)
MetGluSerPheGluGlyGlnGlyAspSerArgGlnSerProAspAsn GluArgGlyAspAsnValGlnThrThrGlyGluHisAspGlnAspPro GlyProGlyProProSerSerGlyAlaSerGluArgLeuValProGlu GluSerTyrSerArgAspGlnGlnProTrpGlyGlnSerArgGlyAsp GluAsnArgGlyTrpMetGlnArgIleArgArgArgArgArgArgArg AlaAlaLeuSerGlyHisLeuLeuAspThrGluAspAsnValProPro TrpLeuProProHisAspIleThrProTyrThrAlaArgAsnIleArg AspAlaAlaCysArgAlaValLysGlnSerHisLeuGlnAlaLeuSer AsnLeuIleLeuAspSerGlyLeuAspThrGlnHisIleLeuCysPhe ValMetAlaAlaArgGlnArgLeuGlnAspIleArgArgGlyProLeu ValAlaGluGlyGlyValGlyTrpArgHisTrpLeuLeuThrSerPro SerGlnSerTrpProMetGlyTyrArgThrAlaThrLeuArgThrLeu ThrProValProAsnArgValGlyAlaAspSerIleMetLeuThrAla ThrPheGlyCysGlnAsnAlaAlaArgThrLeuAsnThrPheSerAla ThrValTrpThrProProHisAlaGlyProArgGluGlnGluArgTyr AlaArgGluAlaGluValArgPheLeuArgGlyLysTrpGlnArgArg TyrArgArgIleTyrAspLeuIleGluLeuCysGlySerLeuHisHis IleTrpGlnAsnLeuLeuGlnThrGluGluAsnLeuLeuAspPheVal ArgPheMetGlyValMetSerSerCysAsnAsnProAlaValAsnTyr TrpPheHisLysThrIleGlyAsnPheLysProTyrTyrProTrpAsn AlaProProAsnGluAsnProTyrHisAlaArgArgGlyIleLysGlu HisValIleGlnAsnAlaPheArgLysAlaGlnIleGlnGlyLeuSer MetLeuAlaThrGlyGlyGluProArgGlyAspAlaThrSerGluThr SerSerAspGluAspThrGlyArgGlnGlySerAspValGluLeuGlu SerSerAspAspGluLeuProTyrIleAspProAsnMetGluProVal GlnGlnArgProValMetPheValSerArgValProAlaLysLysPro ArgLysLeuProTrpProThrProLysThrHisProValLysArgThr AsnValLysThrSerAspArgSerAspLysAlaGluAlaGlnSerThr ProGluArgProGlyProSerGluGlnSerSerValThrValGluPro -continued AlaHisProThrProValGluMetProMetValIleLeuHisGlnPro ProProValProLysProValProLysProThrProProProSer ArgArgArgArgGlyAlaCysValValTyrAspAspAspValIleGlu ValIleAspValGluThrThrGluAspSerSerSerValSerGlnPro AsnLysProHisArgLysHisGlnAspGlyPheGlnArgSerGlyArg ArgGlnLysArgAlaAlaProProThrValSerProSerAspThrGly ProProAlaValGlyProProAlaAlaGlyProProAlaAlaGlyPro ProAlaAlaGlyProProAlaAlaGlyProProAlaAlaGlyProPro AlaAlaGlyProArgIleLeuAlaProLeuSerAlaGlyProProAla AlaGlyProHisIleValThrProProSerAlaArgProArgIleMet AlaProProValValArgMetPheMetArgGluArgGlnLeuProGln SerThrGlyArgLysProGlnCysPheTrpGluMetArgAlaGlyArg GluIleThrGlnMetGlnGlnGluProSerHisLeuGlnSerAla ThrGlnProThrThrProArgProSerTrpAlaProSerValCysAla LeuSerValMetAspAlaGlyLysAlaGlnProIleGluSerSerHis LeuSerSerMetSerProThrGlnProIleSerHisGluGluGlnPro ArgTyrGluAspProAspAlaProLeuAspLeuSerLeuHisProAsp ValAlaAlaGlnProAlaGlnAlaProTyrGlnGlyTyrGlnGlu ProProAlaProGlnAlaProTyrGlnGlyTyrGlnGluProProPro ProGlnAlaProTyrGlnGlyTyrGlnGluProProAlaHisGlyLeu GlnSerSerTyrProGlyTyrAlaGlyProTrpThrProArgSer GlnHisProCysTyrArgHisProTrpAlaProTrpSerGlnAspPro ValHisGlyHisThrGlnGlyProTrpAspProArgAlaProHisLeu ProProGlnTrpAspGlySerAlaGlyHisGlyGlnAspGlnValSer GlnPheProHisLeuGlnSerGluThrGlyProProArgLeuGlnLeu SerLeuValProLeuValSerSerSerAlaProSerTrpSerSerPro GlnProArgAlaProIleArgProIleProThrArgPheProProPro ProMetProLeuGlnAspSerMetAlaValGlyCysAspSerSerGly ThrAlaCysProSerMetProPheAlaSerAspTyrSerGlnGlyAla PheThrProLeuAspIleAsnAlaThrThrProLysArgProArgVal GluGluSerSerHisGlyProAlaArgCysSerGlnAlaThrAlaGlu AlaGlnGluIleLeuSerAspAsnSerGluGluSerValPheProLys AspAlaLysGlnThrAspTyrAspAlaSerThrGluSerGluLeuAsp NS3 (Hepatitis C Virus):

(SEQ ID NO: 22)
AlaProIleThrAlaTyrAlaGlnGlnThrArgGlyLeuLeuGlyCys

IleIleThrGlyLeuThrGlyArgAspLysAsnGlnValGluGlyGlu

ValGlnIleValSerThrAlaAlaGlnThrPheLeuAlaThrCysIle

AsnGlyValCysTrpThrValTyrHisGlyAlaGlyThrArgThrIle

AlaSerSerLysGlyProValIleGlnMetTyrThrAsnValAspGln

-continued

AspLeuValGlyTrpProAlaProGlnGlyAlaArgSerLeuThrPro
CysThrCysGlySerSerAspLeuTyrLeuValThrArgHisAlaAsp
ValIleProValArgArgArgGlyAspGlyArgGlySerLeuLeuSer
ProArgProIleSerTyrLeuLysGlySerSerGlyGlyProLeuLeu
CysProAlaGlyHisAlaValGlyIlePheArgAlaAlaValCysThr
ArgGlyValAlaLysAlaValAspPheIleProValGluGlyLeuGlu
ThrThrMetArgSerProValPheSerAspAsnSerSerProProAla
ValProGlnSerTyrGlnValAlaHisLeuHisAlaProThrGlySer
GlyLysSerThrLysValProAlaAlaTyrAlaAlaGlnGlyTyrLys
ValLeuValLeuAsnProSerValAlaAlaThrLeuGlyPheGlyAla
TyrMetSerLysAlaHisGlyIleAspProAsnIleArgThrGlyVal
ArgThrIleThrThrGlySerProIleThrTyrSerThrTyrGlyLys
PheLeuAlaAspGlyGlyCysSerGlySerAlaTyrAspIleIleIle
CysAspGluCysHisSerThrAspAlaThrSerIleLeuGlyIleGly
ThrValLeuAspGlnAlaGluThrAlaGlyAlaArgLeuThrValLeu
AlaThrAlaThrProProGlySerValThrValProHisProAsnIle
GluGluValAlaLeuSerThrThrGlyGluIleProPheTyrGlyLys
AlaIleProLeuGluAlaIleLysGlyGlyArgHisLeuIlePheCys
HisSerLysLysLysCysAspGluLeuAlaAlaLysLeuValAlaLeu
GlyValAsnAlaValAlaTyrTyrArgGlyLeuAspValSerValIle
ProAlaSerGlyAspValValValValAlaThrAspAlaLeuMetThr
GlyPheThrGlyAspPheAspSerValIleAspCysAsnThrCysVal
ThrGlnThrValAspPheSerLeuAspProThrPheThrIleGluThr
ThrThrLeuProGlnAspAlaValSerArgThrGlnArgArgGlyArg
ThrGlyArgGlyLysProGlyIleTyrArgPheValThrProGlyGlu
ArgProSerGlyMetPheAspSerSerValLeuCysGluCysTyrAsp
AlaGlyCysAlaTrpTyrGluLeuThrProAlaGluThrThrValArg
LeuArgAlaTyrMetAsnThrProGlyLeuProValCysGlnAspHis
LeuGluPheTrpGluGlyValPheThrGlyLeuThrHisIleAspAla
HisPheLeuSerGlnThrLysGlnSerGlyGluAsnLeuProTyrLeu
ValAlaTyrGlnAlaThrValCysAlaArgAlaGlnAlaProProPro
SerTrpAspGlnMetTrpLysCysLeuIleArgLeuLysProThrLeu
HisGlyProThrProLeuLeuTyrArgLeuGlyAlaValGlnAsnGlu
IleThrLeuThrHisProIleThrLysTyrIleMetThrCysMetSer
AlaAspLeuGluValValThr

NS5B (Hepatitis C Virus):

(SEQ ID NO: 23)
GluValTyrGlnCysCysAspLeuGluProGluAlaArgLysValIle
SerAlaLeuThrGluArgLeuTyrValGlyGlyProMetTyrAsnSer
ArgGlyAspLeuCysGlyThrArgArgCysArgAlaSerGlyValPhe
ThrThrSerPheGlyAsnThrLeuThrCysTyrLeuLysAlaSerAla
AlaIleArgAlaAlaGlyLeuLysAspCysThrMetLeuValCysGly
AspAspLeuValValIleAlaGluSerAspGlyValGluGluAspLys
ArgAlaLeuGlyAlaPheThrGluAlaMetThrArgTyrSerAlaPro
ProGlyAspAlaProGlnProAlaTyrAspLeuGluLeuIleThrSer
CysSerSerAsnValSerValAlaHisAspGlyThrGlyLysArgVal
TyrTyrLeuThrArgAspProGluThrProLeuAlaArgAlaAlaTrp
GluThrAlaArgHisThrProValAsnSerTrpLeuGlyAsnIleIle
IleTyrAlaProThrIleTrpValArgMetValLeuMetThrHisPhe
PheSerIleLeuGlnSerGlnGluAlaLeuGluLysAlaLeuAspPhe
AspMetTyrGlyValThrTyrSerIleThr

E1 (Hepatitis C Virus):

(SEQ ID NO: 24)
TyrGlnValArgAsnSerSerGlyLeuTyrHisValThrAsnAspCys
ProAsnSerSerIleValTyrGluThrAlaAspIleLeuHisSerPro
GlyCysValProCysValArgGluGlyAsnThrSerLysCysTrpVal
AlaValAlaProThrValAlaThrLysAspGlyLysLeuProThrThr
GlnLeuArgHisIleAspLeuLeuValGlyAlaThrLeuCysSerAla
LeuTyrValGlyAspLeuCysGlySerValPheLeuValSerGlnLeu
PheThrPheSerProArgHisTrpThrThrGlnAspCysAsnCysSer
IleTyrProGlyHisValThrGlyHisArgMetAlaTrpAspMetMet
MetAsnTrpSerProThrThrAlaLeuValValAlaGlnLeuLeuArg
ValProGlnAlaIleLeuAspMetIleAlaGlyAlaHisTrpGlyVal
LeuAlaGlyIleAlaTyrPheSerMetValGlyAsnTrpAlaLysVal
LeuValValLeuLeuLeuPheAlaGlyValAspAla

E2 (Hepatitis C Virus)

(SEQ ID NO: 25)
HisTrpGlyValMetPheGlyLeuAlaTyrPheSerMetGlnGlyAla
TrpAlaLysValIleValIleLeuLeuLeuThrAlaGlyValAspAla
SerSerHisAsnThrArgThrValGlyGlyGlnIleAlaArgGlnLeu
GlnProPheThrArgLeuPheSerValGlyProAsnGlnAsnIleGln
LeuIleAsnThrAsnGlySerTrpHis

HBsAg (Hepatitis B Virus)

(SEQ ID NO: 26)
SerThrThrSerThrGlyProCysArgThrCysMetThrThrAlaGln
GlyThrSerMetTyrProSerCysCysCysThrLysProSerAspGly
AsnCysThrCysIleProIleProSerSerTrpAlaPheGlyLysPhe
LeuTrpGluTrpAlaSerAlaArgPhe

Pre-S1 Protein (Hepatitis B Virus)

(SEQ ID NO: 27)

MetGlyGlnAsnLeuSerValSerAsnProLeuGlyPhePheProGlu

HisGlnLeuAspProLeuPheLysAlaAsnSerAsnAsnProAspTrp

AspPheAsnProAsnLysAspAsnTrpProGluAlaThrGlnValGly

ValGlyAlaPheGlyProGlyPheThrProProHisGlyGlyLeuLeu

GlyTrpSerSerGlnAlaGlnGlyAlaIleThrThrLeuProAlaVal

ProProSerAlaAlaThrAsnArg

Pre-S2 Protein (Hepatitis B Virus)

(SEQ ID NO: 28)

IleSerSerIlePheSerArgIleGlyAspProAlaLeuAsnMetGlu

AsnIleThrSerGlyPheLeuGlyProLeuLeuValLeuGlnAlaGly

PhePheLeuLeuThrArgIleLeuThrIleProGlnSerLeuAspSer

TrpTrpThrSerLeuAsnPheLeuGlyGlyThrThrValCysLeuGly

GlnAsnSerGlnSerProThrSerAsnHisSerProThrSerCysPro

ProThrCysProGlyTyrArgTrpMetCysLeuArgArgPheIleIle

PheLeuPheIleLeuLeuLeuCysLeuIlePheLeuLeuValLeuLeu

AspTyrGlnGlyMetLeuProValCysProLeuIleProGlySerSer

ThrThrSerThrGlyProCysArgThrCysThrThrProAlaGlnGly

ThrSerMetTyrProSerCysCysCysThrLysProSerAspGlyAsn

CysThrCysIleProIleProSerSerTrpAlaPheGlyLysPheLeu

TrpGluTrpAlaSerAlaArgPheSerTrpLeuSerLeuLeuValPro

PheValGlnTrpPheValGlyLeuSerProThrValTrpLeuSerVal

IleTrpMetMetTrpTyrTrpGlyProSerLeuTyr

Envelope Glycoprotein B, gB (Human Cytomegalovirus CMV)

(SEQ ID NO: 29)

TyrAsnLysProIleAlaAlaArgPheMetGlyAspValLeuGlyLeu

AlaSerCysValThrIleAsnGlnThrSerValLysValLeuArgAsp

MetAsnValLysGluSerProGlyArgCysTyrSerArgProValVal

IlePheAsnPheValAsnSerSerTyrValGlnTyrGlyGlnLeuGly

GluAspAsnGluIleLeuLeuGlyAsnHisArgThrGluGluCysGln

PheProSerLeuLysIlePheIleAlaGlyAsnSerAlaTyrGluTyr

ValAspTyrLeuPheLysArgMetIleAspLeuSerSerIleTyrThr

ValAspSerMetIleAlaLeuAspIleAspProLeuGluAsnThrAsp

PheArgValLeuGluLeuTyrSerGlnLysGluLeuArgSerSerAsn

ValPheAspLeuGluGluIleMetArgGluPheAsnSerTyrLysGln

ArgValLysTyrValGluAspLysValValAspProLeuProPro pp65 (Human Herpesvirus 5 and Human Cytomegalovirus CMV)

(SEQ ID NO: 30)

MetAlaSerValLeuGlyProIleSerGlyHisValLeuLysAlaVal

PheSerArgGlyAspThrProValLeuProHisGluThrArgLeuLeu

GlnThrGlyIleHisValArgValSerGlnProSerLeuIleLeuVal

SerGlnTyrThrProAspSerThrProCysHisArgGlyAspAsnGln

LeuGlnValGlnHisThrTyrPheThrGlySerGluValGluAsnVal

SerValAsnValHisAsnProThrGlyArgSerIleCysProSerGln

GluProMetSerIleTyrValTyrAlaLeuProLeuLysMetLeuAsn

IleProSerIleAsnValHisHisTyrProSerAlaAlaGluArgLys

HisArgHisLeuProValAlaAspAlaValIleHisAlaSerGlyLys

GlnMetTrpGlnAlaArgLeuThrValSerGlyLeuAlaTrpThrArg

GlnGlnAsnGlnTrpLysGluProAspValTyrTyrThrSerAlaPhe

ValPheProThrLysAspValAlaLeuArgHisValValCysAlaHis

GluLeuValCysSerMetGluAsnThrArgAlaThrLysMetGlnVal

IleGlyAspGlnTyrValLysValTyrLeuGluSerPheCysGluAsp

ValProSerGlyLysLeuPheMetHisValThrLeuGlySerAspVal

GluGluAspLeuThrMetThrArgAsnProGlnProPheMetArgPro

HisGluArgAsnGlyPheThrValLeuCysProLysAsnMetIleIle

LysProGlyLysIleSerHisIleMetLeuAspValAlaPheThrSer

HisGluHisPheGlyLeuLeuCysProLysSerIleProGlyLeuSer

IleSerGlyAsnLeuLeuMetAsnGlyGlnGlnIlePheLeuGluVal

GlnAlaIleArgGluThrValGluLeuArgGlnTyrAspProValAla

AlaLeuPhePhePheAspIleAspLeuLeuLeuGlnArgGlyProGln

TyrSerGluHisProThrPheThrSerGlnTyrArgIleGlnGlyLys

LeuGluTyrArgHisThrTrpAspArgHisAspGluGlyAlaAlaGln

GlyAspAspAspValTrpThrSerGlySerAspSerAspGluGluLeu

ValThrThrGluArgLysThrProArgValThrGlyGlyGlyAlaMet

AlaGlyAlaSerThrSerAlaGlyArgLysArgLysSerAlaSerSer

AlaThrAlaCysThrAlaGlyValMetThrArgGlyArgLeuLysAla

GluSerThrValAlaProGluGluAspThrAspGluAspSerAspAsn

GluIleHisAsnProAlaValPheThrTrpProProTrpGlnAlaGly

IleLeuAlaArgAsnLeuValProMetValAlaThrValGlnGlyGln

AsnLeuLysTyrGlnGluPhePheTrpAspAlaAsnAspIleTyrArg

IlePheAlaGluLeuGluGlyValTrpGlnProAlaAlaGlnProLys

ArgArgArgHisArgGlnAspAlaLeuProGlyProCysIleAlaSer

ThrProLysLysHisArgGly

IE-1 Protein (Human Herpesvirus 5, and Human Cytomegalovirus CMV)

```
                                          (SEQ ID NO: 31)
MetGluSerSerAlaLysArgLysMetAspProAspAsnProAspGlu

GlyProSerSerLysValProArgProGluThrProValThrLysAla

ThrThrPheLeuGlnThrMetLeuArgLysGluValAsnSerGlnLeu

SerLeuGlyAspProLeuPheProGluLeuAlaGluGluSerLeuLys

ThrPheGluGlnValThrGluAspCysAsnGluAsnProGluLysAsp

ValLeuAlaGluLeuValLysGlnIleLysValArgValAspMetVal

ArgHisArgIleLysGluHisMetLeuLysLysTyrAlaGlnThrGlu

GluLysPheThrGlyAlaPheAsnMetMetGlyGlyCysLeuGlnAsn

AlaLeuAspIleLeuAspLysValHisGluProPheGluGluMetLys

CysIleGlyLeuThrMetGlnSerMetTyrGluAsnTyrIleValPro

GluAspLysArgGluMetTrpMetAlaCysIleLysGluLeuHisAsp

ValSerLysGlyAlaAlaAsnLysLeuGlyGlyAlaLeuLysAlaLys

AlaArgAlaLysLysAspGluLeuArgArgLysMetMetTyrMetCys

TyrArgAsnIleGluPhePheThrLysAsnSerAlaPheProLysThr

ThrAsnGlyCysSerGlnAlaMetAlaAlaLeuGlnAsnLeuProGln

CysSerProAspGluIleMetSerTyrAlaGlnLysIlePheLysIle

LeuAspGluGluArgAspLysValLeuThrHisIleAspHisIlePhe

MetAspIleLeuThrThrCysValGluThrMetCysAsnGluTyrLys

ValThrSerAspAlaCysMetMetThrMetTyrGlyGlyIleSerLeu

LeuSerGluPheCysArgValLeuCysCysTyrValLeuGluGluThr

SerValMetLeuAlaLysArgProLeuIleThrLysProGluValIle

SerValMetLysArgArgIleGluGluIleCysMetLysValPheAla

GlnTyrIleLeuGlyAlaAspProLeuArgValCysSerProSerVal
```

```
                          -continued
AspAspLeuArgAlaIleAlaGluGluSerAspGluGluAspAlaIle AlaAlaTyrThrLeuAlaThrAlaGlyAlaSerSerSerAspSerLeu ValSerProProGluSerProValProAlaThrIleProLeuSerSer ValIleValAlaGluAsnSerAspGlnGluGluSerGluGlnSerAsp GluGluGlnGluGluGlyAlaGlnGluGluArgGluAspThrValSer ValLysSerGluProValSerGluIleGluGluValAlaSerGluLys GluGluAspGlyAlaGluGluProThrThrSerGlyGlyLysSerThr HisProMetValThrArgSerLysAlaAspGln
```

IE-2 Protein (Human Herpesvirus 5 and Human Cytomegalovirus CMV):

```
                                          (SEQ ID NO: 32)
MetLysProValLeuValLeuAlaIleLeuAlaValLeuPheLeuArg

LeuAlaAspSerValProArgProLeuAspValValValSerGluIle

ArgSerAlaHisPheArgValGluGluAsnGlnCysTrpPheHisMet

GlyMetLeuTyrPheLysGlyArgMetSerGlyAsnPheThrGluLys

HisPheValAsnValGlyIleValSerGlnSerTyrMetAspArgLeu

GlnValSerGlyGluGlnTyrHisHisAspGluArgGlyAlaTyrPhe

GluTrpAsnIle
```

A fusion protein of one of the above-mentioned antigen with the N-terminal portion of Ag473 can be produced at unexpected high yield in an *E. coli* expression system. It was also unexpected that the recombinant fusion protein can induce immune responses against the antigen and related disorders, such as cancer.

The just-mentioned Ag473 is a *Neisseria Mengitidis* lipoprotein consisting of four domains, SP and Domains 1-3. Shown below is its amino acid sequence with the four domains identified:

(SEQ ID NO: 7)

Met Lys Lys Leu Leu Ile Ala Ala Met Met Ala Ala Ala Leu Ala Ala Cys Ser Gln Glu Ala Lys Gln Glu Val
Lys Glu Ala Val Gln Ala Val Glu Ser Asp Val Lys Asp Thr Ala Ala Ser Ala Ala Glu Ser Ala Ala Ser Ala
Val Glu Glu Ala Lys Asp Gln Val Lys Asp Ala Ala Ala Asp Ala Lys Ala Ser Ala Glu Glu Glu *Ala Val Thr*
*Glu Ala Lys Glu Ala Val Thr Glu Ala Lys Glu Ala Val Thr Glu Ala Lys Glu Ala Val Thr Glu Ala Ala Lys*
*Asp Thr Leu Asn Lys Ala Ala Asp Ala Thr Gln Glu Ala Ala Asp Lys Met Lys Asp Ala Ala Lys*

SP: amino acid residues 1-17 (underlined, SEQ ID NO: 8)
Domain 1: amino acid residues 18-40 (highlited, SEQ ID NO: 9)
Domain 2: amino acid residues 41-71 (bold face, SEQ ID NO: 10)
Domain 3: amino acid residues 72-121 (italic, SEQ ID NO: 11)

The term "lipidating sequence" refers to a non-naturally occurring amino acid sequence that (a) includes a first fragment that is at least 80% (85%, 90%, 95%, or 99%) identical to SP or Ag473 and a second fragment at least 80% (85%, 90%, 95%, or 99%) identical to Domain 1 of Ag473, the first fragment being at the N-terminus of the lipidating sequence, and (b) facilitates lipidation in *E. coli* of a polypeptide or protein carrying the lipidating sequence at its N-terminus. In the lipidating sequence, the first fragment is linked to the second fragment either directly or via a peptide linker. Preferably, this sequence has a length of 40-100 (e.g., 40-80) amino acids. In one example, the lipidating sequence includes SP and Domain 1, i.e., aa 1-40 of SEQ ID NO: 7 (SEQ ID NO: 12). Additional examples of the lipidating sequence include any other fragments of SEQ ID NO: 7 that include aa 1-40, e.g., 1-41, 1-45, 1-50, 1-60, 1-80, 1-100, and 1-121 or SEQ ID NO: 7.

As used herein, "percent homology" of two amino acid sequences is determined using the algorithm described in Karlin and Altschul, *Proc, Natl. Acad. Sci. USA* 87:2264-2268, 1990, modified as described in Karlin and Altschul, *Proc, Natl. Acad. Sci. USA* 90:5873-5877, 1993. Such an algorithm is incorporated into the NBLAST and XBLAST programs of Altschul et al., *J. Mol. Biol.* 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used.

A polypeptide or fusion protein of the invention can be obtained as a synthetic polypeptide or a recombinant polypeptide. To prepare a recombinant polypeptide, a nucleic acid encoding it can be linked to another nucleic acid encoding a fusion partner, e.g., Glutathione-S-Transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

In the present invention, the lipidating sequence mentioned above is linked to a tumor-associated antigen, such as a viral antigen derived from HPV (e.g., HPV E7) forming a fusion protein, which is in lipidated form when expressed in *E. coli* by conventional recombinant technology. An example follows. A DNA fragment encoding the lipidating sequence and a DNA fragment encoding the Elm are inserted into an expression vector, preferably carrying a strong promoter (e.g. T7, T5, T3, or SP6), to construct an expression plasmid. The strong promoter can be inducible, e.g., by isopropyl β-D-thiogalactoside (IPTG). The expression plasmid is then introduced into an *E. coli* host strain and positive transformants are cultured under suitable conditions for protein expression. It is preferred that the *E. coli* host strain be resistant to the toxic effects induced by over-expression of exogenous proteins. Such *E. coli* strains can be identified/generated by the methods described in U.S. Pat. No. 6,361,966. Examples of these *E. coli* strains include, but are not limited to, C43(DE3) (ECCC B96070445), C41(DE3) (ECCC B96070444), C0214 (DE3), DK8(DE3)S (NCIMB 40885), and C2014(DE3) (NCIMB 40884).

Preferably, the fusion protein thus expressed is isolated from the *E. coli* host cells and its lipidation status is confirmed via methods known in the art, e.g., immunoblotting with an anti-lipoprotein antibody or mass spectrometry.

A polypeptide or fusion protein of this invention can be used to prepare an immunogenic composition (e.g., a vaccine) for generating antibodies against, e.g., HPV in a subject (e.g., a human subject) susceptible to the virus. Such compositions can be prepared, e.g., in the manners described below, or by any other equivalent methods known in the art.

This polypeptide or lipidated fusion protein can be mixed with a pharmaceutically acceptable carrier such as a phosphate buffered saline, a bicarbonate solution, or an adjuvant to produce a pharmaceutical composition. The carrier must be "acceptable" in the sense that it is compatible with the active ingredient of the composition, and preferably, capable of stabilizing the active ingredient and not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. In one example, the polypeptide or fusion protein is mixed with an adjuvant to form a composition useful for immune modulation. This composition may be prepared as injectables, as liquid solutions or emulsions. See U.S. Pat. Nos. 4,601,903; 4,599,231; 4,599,230; and 4,596,792.

An "adjuvant" refers to a substance added to an immunogenic composition, such as a vaccine, that while not having any specific antigenic effect in itself, can stimulate the immune system and increase the immune response to the immunogenic composition. Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing *Corynebacterium parvum* and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery. See Audran et al. Vaccine 21:1250-5, 2003; and Denis-Mize et al. Cell Immunol., 225:12-20, 2003. Alternatively, the fusion protein of the invention can be used in a vaccine without any adjuvant.

An effective amount of the composition described above may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders. An "effective amount" means that amount of a composition that elicits a biological or medicinal response in a tissue system of a subject, or in a subject, that is being sought by a researcher, veterinarian, medical doctor or other clinician.

The above-described polypeptide and fusion protein can be used in an immunogenic composition, e.g., a vaccine, for generating antibodies and immune response against virus in a subject susceptible to the virus. A vaccine can be administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

The term "immune response" or "immunogenic response" refers to any reaction of the immune system in response to an antigen in a subject. Examples of an immune response in a vertebrate include, but are not limited to, antibody production, induction of cell-mediated immunity, and complement activation. The immune response to a subsequent stimulus by the same antigen, also named the secondary immune response, is more rapid than in the case of the primary immune response. The term "immunogenic" refers to a capability of producing an immune response in a host animal against an antigen or antigens. This immune response forms the basis of the protective immunity elicited by a vaccine against a specific infectious organism.

An "antigen" refers to a molecule containing one or more epitopes that will stimulate a host's immune system to make a humoral and/or cellular antigen-specific response. The term "antigen" is used interchangeably with "immunogen." As a result of coming in contact with appropriate cells, an antigen induces a state of sensitivity or immune responsiveness and reacts in a demonstrable way with antibodies or immune cells of the sensitized subject in vivo or in vitro. An antigen can be specifically recognized and bound by antibodies in an organism. An antigen in association with a major histocompatibility complex (MHC) can also be recognized and bound by receptors on the surface of T lymphocytes (T-cells), leading to the activation of the T-cells. The term "epitope" as used herein refers to the site on an antigen to which a specific antibody molecule or a T-cell receptor binds. The term is used herein interchangeably with "antigenic determinant" or "antigenic determinant site."

An "antibody" refers to an immunoglobulin molecule or at least one immunologically active portion of an immunoglobulin molecule that has a specific amino acid sequence and binds only to an antigen or a group of antigens that are closely related. Examples of antibodies include IgG, IgM, IgA, IgD and IgE. Examples of immunologically active portions of immunoglobulin molecules include Fab and F(ab)'.sub.2 fragments which can be generated by treating the antibody with an enzyme such as pepsin. An antibody can be a monoclonal antibody or a polyclonal antibody. The term "monoclonal antibody" refers to a population of antibody molecules that contains only one species of an antigen binding site and that is capable of immunoreacting with a particular epitope. The term "polyclonal antibody" refers to a population of antibody molecules that contains more than one species of antigen binding sites and that is capable of immunoreacting with more than one epitope on the polypeptide.

A subject susceptible to virus infection can be identified by methods known in the art and administered a composition of the invention. The dose of the composition depends, for example, on the particular polypeptide/protein, whether an adjuvant is co-administered, and the type of adjuvant co-administered, the mode and frequency of administration, as can be determined by one skilled in the art. Administration is repeated as necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the composition against the virus. Methods of assaying antibodies or cytotoxic T cells against a protein or infection are well known in the art. Additional boosters can be given as needed. By varying the amount of polypeptide/protein, the dose of the composition, and frequency of administration, the immunization protocol can be optimized for eliciting a maximal immune response. Before a large scale administering, efficacy testing is desirable. In an efficacy testing, a non-human subject (e.g., mouse, rat, rabbit, house, pig, cow, or monkey) can be administered via an oral or parenteral route with a composition of the invention. After the initial administration or after optional booster administration, both the test subject and the control subject (receiving mock administration) can be challenged with virus to test the efficacy of the composition.

Various antigens can be used. In certain embodiments, the antigen may be a tumor-associated antigen, a cancer antigen, or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, aml1, Prostate Specific Antigen (PSA) and its antigenic epitopes PSA-1, PSA-2, and PSA-3, prostate-specific membrane antigen (PSMA), T-cell receptor/ CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGS, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, α-catenin, β-catenin, γ-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/ GA733, APC), choriocarcinoma (CEA), epithelial cell cancer (cyclophilin b), gastric cancer (HER2/neu, c-erbB-2, ga733 glycoprotein), hepatocellular cancer (α-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus, testicular cancer (NY-ESO-1), and T cell leukemia (HTLV-1 epitopes), and viral products or proteins.

As mentioned above, viral infection causes various disorders, including cancer. Examples of cancer-causing virus include EBV, HPV, HCV, HBV, and CMV. Among them. HPV is known to cause disorders including warts (e.g., genital warts), cervical dysplasia, and cancer (e.g., cervical cancer). Accordingly, within the scope of this invention is an immunogenic composition against HPV infection and related disorders. A number of HPV antigens can be used. HPV genotypes correlated to carcinogenic ability are classified as high-risk types that include type 16, 18, 31, 33, 35, 39, 45, 51, 52, 56, 58, 59, 68, 73, and 82 (Munoz et al., *N Engl J Med* 348:518-27, 2003). Those of 1-HPV16 and HPV18 are particular useful as they are the two with high prevalence in invasive cervical cancer (Bosch et al., *J Natl Cancer Inst* 87:796-802, 1995). The HPV16 was detected in 50% of cervical cancer, and HPV18 was associated with 18% of cervical cancer. In adeno- and adenosquamous-carcinoma, HPV prevalence was significantly lower (76.4%) than in squamous cell carcinoma (87.3%), and HPV18 was the predominant types (~40%) (Clifford et al., *Br J Cancer* 89:101-5, 2003). Several clinical trials have been conducted for vaccine therapy in treating patients with HPV-associated tumors. Most of them were based on either E7 or E7/E6 oncoproteins because E6 and E7 are consistently expressed in premalignancies and malignancies. Moreover, the importance of cell-mediated immune responses, to these proteins is well documented (Moscicki, *J Adolesc Health* 43:S26-40, 2008).

As described below in the example, inactive HPV oncoproteins (e.g. inactive E7 (E7m)) could be fused with the D1 of Ag473 to produce recombinant lipo-immunogen (rlipo-E7m). In TC-1 mouse model, the rlipo-E7m protected the mice against the challenge of tumor cells. These results clearly demonstrated that the rlipo-E7m is useful as a potential vaccine against HPV-associated tumors and implied that the lipo-immunogens approach can be applied to HPV oncoproteins such as E7 and E6 against HPV-associated tumors.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example

Expression of Lipidated Fusion Protein, rlipo-E7m

The E7m gene was obtained using an assembly PCR method with overlapping primers. The product of the assembly PCR was then amplified by conventional PCR (Dillon P J, Rosen C A. Biotechniques 1990; 9: 298, 300). The forward primer for this step, 5'-GGAATTCCATATGCACGGC-GATACCCCGACCCTGC-3' (SEQ ID NO: 3), included an Nde I site (underlined), and the reverse primer, 5'-AGAGCCGCTCGAG CGGTTTCTGGCTCGCAATCGG-3' (SEQ ID NO: 4), included an Xho I site (underlined). The PCR product was cloned into the expression vector pET-22b (+) (NOVAGEN, Madison, Wis.); using Nde I and Xho I sites, to produce the pE7m plasmid. As a result, the C-terminal end of the recombinant protein contained an additional hexahistidine tag (HisTag).

The expression plasmid pE7m was transformed into *E. coli* strain BL21Star (DE3) (INVITROGEN, USA) for protein expression. The transformed cells were cultured at 37° C. overnight and then induced with 1 mM of IPTG for 3 h. To obtain the plasmid for expressing lipidated immunogen, we modified the plasmid, pD1E3, which can be transformed into CD43(DE3) strain for expression of recombinant lipoprotein, rlipo-D1E3 (Chen et al., Vaccine 2009; 27: 1400-9). The forward primer for this step, 5'-CGCGGATCCATGCA-CGGCGATACCCCGACCCT-3' (SEQ ID NO: 5), included a Bam HI site (underlined), and the reverse primer, 5'-AGAGCCG CTCGAGCGGTTTCTGGCTCGCAATCGG-3' (SEQ ID NO: 6), included an Xho I site (underlined). The PCR product was cloned into pDIE3, using Bam HI and Xho I sites to produce the plipo-E7m plasmid. As a result, the C-terminal end of the recombinant protein contains an additional hexahistidine tag (HisTag). The expression plasmid, plipo-E7m, was transformed into *E. coli* strain C43(DE3) (INVITROGEN, Carlsbad, Calif.) for lipo-protein expression. The transformed cells were cultured at 37° C. overnight and then induced with 1 mM of IPTG at 12° C. for 3 days.

Characterization of rlipo-E7m

Recombinant E7m (rE7m), expressed from pE7m, and rlipo-E7m, expressed from plipoE7m, were isolated from C43(DE3) cells by immobilized metal affinity chromatography (IMAC) as follows. E. coli cells were harvested from 4-liter cell cultures by centrifugation (8000×g for 20 min) and the pellets thus collected were re-suspended in 100 ml of a homogenization buffer containing 50 mM Tris (PH8.0). The E. coli cells were then disrupted using a French Press (CONSTANT SYSTEMS, Daventry. UK) at 27 Kpsi in the presence of a detergent and the cell lysates thus obtained were centrifuged at 80,000×g for 60 min. The pellet was collected and solubilized using extraction buffer (1% TRITON X-100/50 mM Tris (PH8.9)). After centrifugation at 80000×g for 40 min, the supernatant were incubated with 5 ml Ni-NTA resin (QIAGEN, San Diego, Calif., USA) at cold room overnight. The incubated sample and resin slurry were loaded onto a column (1.6 cm i.d.×2.7 cm). The column was washed first with 50 mL of an extraction buffer. After recombinant proteins were eluted with the elution buffer (1% TRITON X-100, 50 mM Tris (PH8.9), they were characterized by both SDS-PAGE and immunoblotting. The results (shown in FIG. 2) indicated that recombinant lipo-E7m were isolated with high purity. The removal of lipopolysaccharide (LPS) was achieved using IMAC coupled with copper ions and extensively washed with 1000 mL of the elution buffer and 300 mL of a washing buffer (100 mM imidazole, 1% TRITON X-100, 50 mM Tris (PH8.9)). The residue of LPS in the preparation was less than 30 EU/mg.

Fusion protein lipo-E7m was then subjected to mass spectrometry (MS) analysis as described below. Specifically, the purified rlipo-E7m was infused into a WATERS SYNAPT HDMS mass spectrometer using a manual acquisition mode. The molecular mass was calculated using the maximum entropy algorithm MaxEnt1 (WATERS) for 15 iterations. To identify the N-terminal fragment of rlipo-E7m, rlipo-E7m was first dialyzed against 5 mM ammonium bicarbonate at pH 8.5 and then treated with trypsin (PROMEGA Co., Madison, Wis.) at a lipo-E7m:trypsin ratio of 50:1 (Wt/Wt) in 25 mM ammonium bicarbonate (pH 8.5) for 5 min at room temperature. The enzymatic reaction was terminated by addition of formic acid (final concentration 1.2%). The reaction mixture was further polished using ZIPTIP (MILLIPORE). One microliter of the typsin-digested protein was mixed with 1 μl of a saturated solution of α-ciano-4-hydrozycinnamic acid (SIGMA) in acetonitrile/0.1% trifluoroacetic acid (1:3, vol/vol). One microliter of the mixture was placed on the target plate of a matrix-assisted laser desorption ionization time-of-flight (MALDI-TOF) mass spectrometer (BURKER) for analysis. Results obtained from MALDI-TOF analysis as described above indicated that the partial trypsin digestion products corresponded to the N-terminal fragments of rlipo-E7m and these peptides were lipidated.

As shown in FIG. 3A, the LC/MS result demonstrated that there were at least five different modifications of the purified rlipo-E7m and each modification is different by 14 amu. Molecular masses (in daltons) determined by the maximum entropy algorithm (MaxEnt1) were given. It demonstrated that there are five major peaks, 15384.5, 15400, 15412.5, 15426, 15439, respectively. As shown in FIG. 3B, 10 minute-digested sample was analyzed by Bruker AutoFlex III mass spectrometer. The MALDI-TOF MS spectra also demonstrated that there are five peaks at m/z 1452, 1466, 1480, 1492, 1506, respectively, which are the signature of lipidated derivatives.

The above results were unexpected since E. coli was generally viewed as not suitable for producing modified proteins, particularly, lipidated proteins.

Cytotoxic T Lymphocyte Assay

To investigate whether rlipo-E7m immunization could induce cytotoxic T lymphocytes in vivo, C57BL/6 mice were immunized with rE7m or rlipo-E7m proteins, and cytotoxic T lymphocytes activity was analyzed using Chromium release assay as described below.

Briefly, C57BL/6 mice were immunized with PBS, rE7m (30 mg), or rlipo-E7m (30 mg) s.c. on day 0 and day 14. On day 21, splenocytes from the mice in each group were collected and re-stimulated with 1 mg/ml RAH in 10% FBS RPMI in the presence of 10 U/ml IL-2 for 5 days as effector cells. Seven days after the last immunization, erythrocyte-depleted splenocytes ($1 \times 10^6$ cells/mL) were cultured in vitro with 1 mg/mL of HPV16 E7-derived peptide RAH, i.e., RAHYSIVTF (SEQ ID NO: 33), and 10 U/mL of recombinant human IL-2 in 24-well plates for 5 days. The TC-1 cells ($5 \times 10^5$) were labeled with 100 mCi of $^{51}$Cr (Na$_2^{51}$CrO$_4$; PERKINELMER, Waltham, Mass., USA) at 37° C. for 1 hr to serve as target cells. The peptide-stimulated splenocytes were mixed with labeled target cells at various effector-to-target ratios as indicated. After 4-hr incubation at 37° C., the radioactivity of the supernatant was measured using a gamma counter (PERKINELMER). The percentage of specific lysis was calculated using the following equation: 100×[(experimental release−spontaneous release)/(maximal release−spontaneous release)].

As shown in FIG. 4, rlipo-E7m could induce stronger killing effect on E7-expressed tumor (TC-1 cells) than rE7m in the Err ratio at 100 and 50. These results indicated that rlipo-E7m immunization could induce CTL responses in vivo.

In Vivo Tumor Protection Experiments

For in vivo tumor protection experiment, C57BL/6 mice (six per group) were immunized with 30 μg of rE7m or rlipo-E7m. The mice were boosted twice with the same regimen as that used in the first vaccination. Two week after the last vaccination, the mice were challenged with $2 \times 10^5$ TC-1 tumor cells/mouse subcutaneously in the right leg and monitored twice a week by inspection and palpation: Another animal model was injected with $2 \times 10^5$ TC-1 tumor cells/mouse first. On the seventh day, 30 μg of rE7m or rlipo-E7m were administrated to C57BL/6 mice (six per group). These mice were monitored twice a week by inspection and palpation.

Figure 5A:
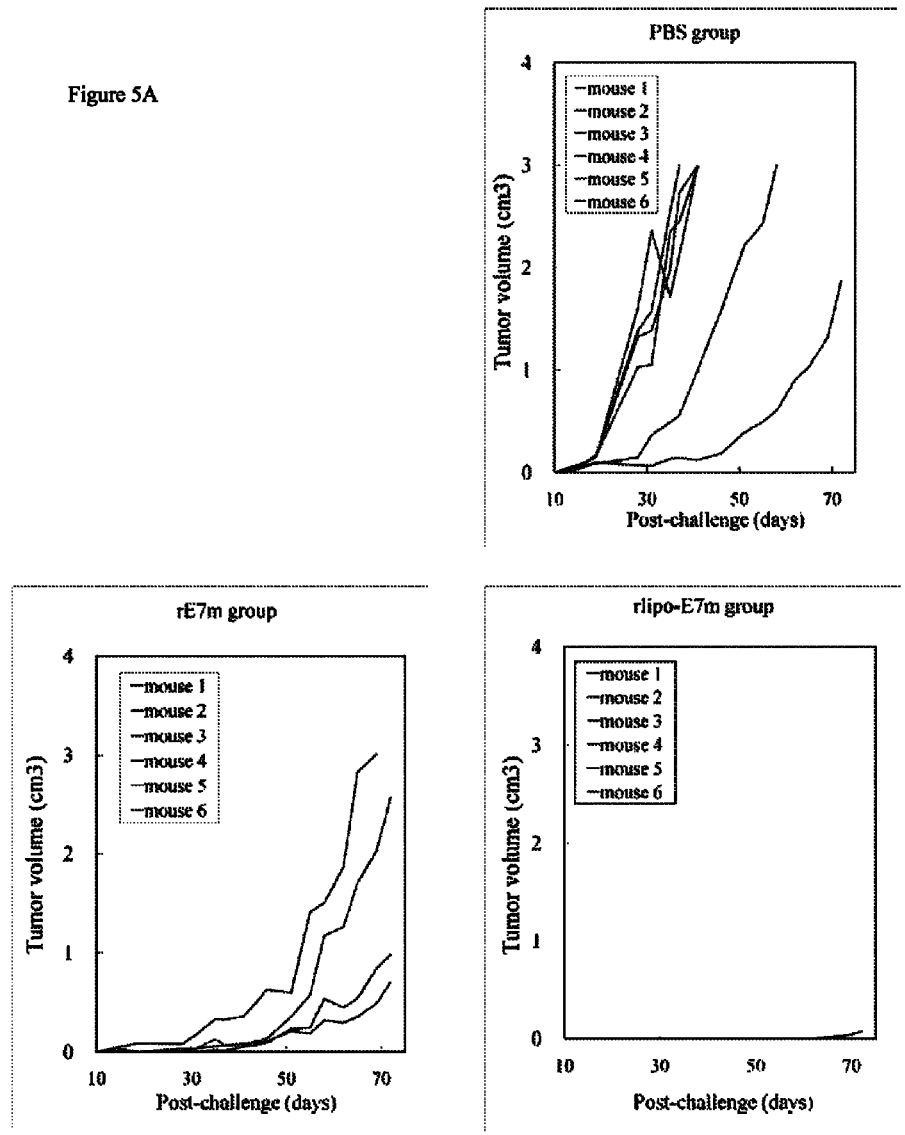
FIGS. 5A and 5B are diagrams showing effects of rlipo-E7m in protecting mice from tumor as compared with rE7m.
Figure 5B:
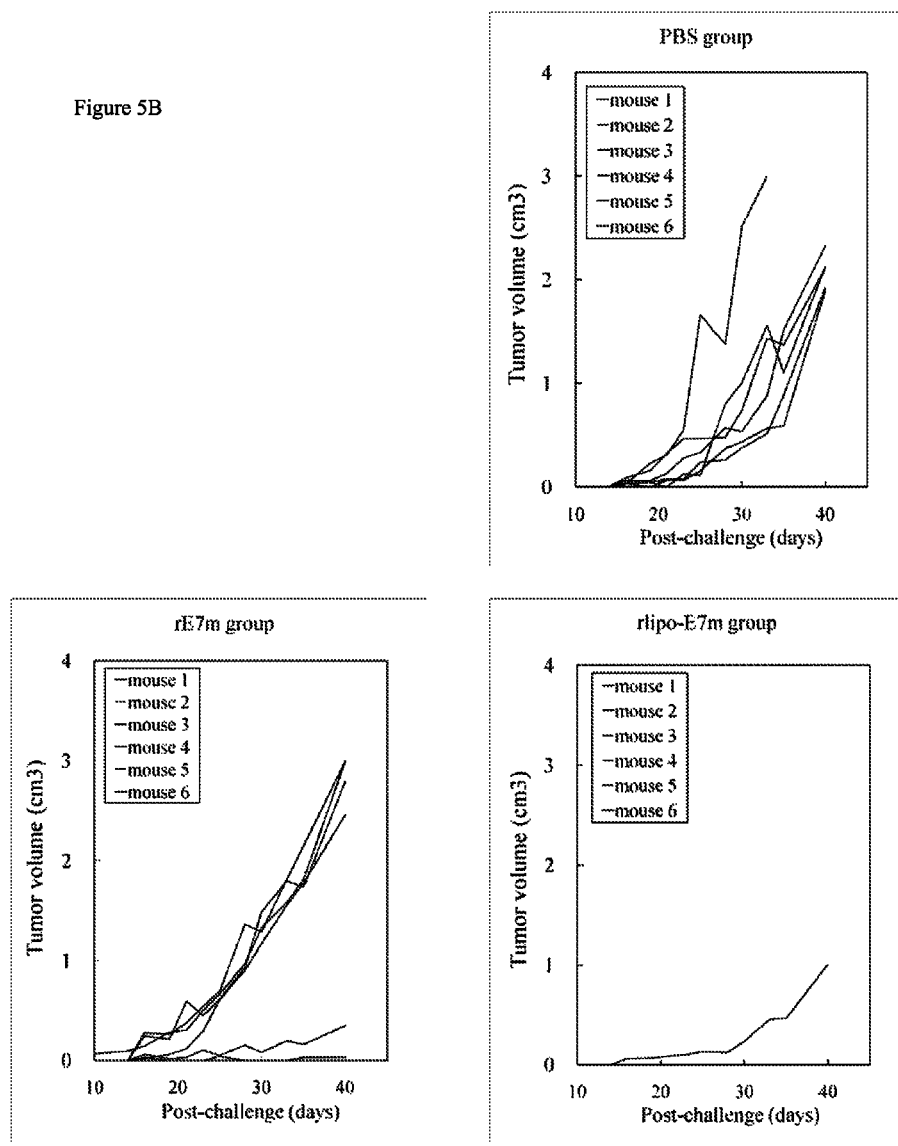

As shown in FIG. 5A, the mice were vaccinated with immunogens and then, were challenged using TC-1 tumor cells. After vaccinated with rlipo-E7m, 100% of mice remained tumor free over 60 days after tumor injection, while those injected with PBS developed tumor within 20 days and 67% of mice were developed tumor after vaccinated with rE7m. FIG. 5B demonstrated that, in the mice injected with tumor cells before administrating the immunogens, rlipo-E7m still showed a superior efficacy than its non-lipidated counterpart, rE7m. Specifically, 83% of those receiving rlipo-E7m remained tumor free, while all the mice injected with PBS developed tumor within 20 days and only 18% of the mice receiving rE7m remain tumor free. These results demonstrated that in both mouse models, the efficacy of inactive-E7 was dramatically increased in its lipidated form. The mice vaccinated with rlipo-E7m provided significant protection against TC-1 cell challenge when compared to that vaccinated with rE7m.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. A number of embodiments of the invention have been described. Nevertheless, it will be understood that various modifications may be made without departing from the spirit and scope of the invention. Accordingly, other embodiments are within the scope of the following claims.

What is claimed is:

1. An isolated polypeptide comprising the sequence of SEQ ID NO.: 2.

2. An isolated nucleic acid comprising a sequence encoding the polypeptide of claim 1 or a complement thereof.

3. The nucleic acid of claim 2, wherein the nucleic acid contains the sequence of SEQ ID NO: 13.

4. An expression vector comprising the nucleic acid of claim 2.

5. An isolated host cell comprising the nucleic acid of claim 2.

6. The host cell of claim 5, wherein the host cell is an *E. coli* cell.

7. An immunogenic composition comprising a polypeptide of claim 1.

8. The immunogenic composition of claim 7, wherein the composition further comprises a pharmaceutically acceptable adjuvant.

9. A method of inducing an immune response in a subject against human papillomavirus (HPV), comprising administering to a subject in need thereof an effective amount of a composition containing a polypeptide of claim 1.

10. A method of producing a polypeptide, comprising
   culturing a host cell comprising the nucleic acid of claim 2 in a medium under conditions permitting expression of a polypeptide encoded by the nucleic acid, and
   purifying the polypeptide from the cultured cell or the medium.

11. An isolated fusion protein, comprising
   a first segment having a lipidating sequence and
   a second segment having the sequence of SEQ ID NO: 2, wherein the first segment is located at the N-terminus to the second segment in the fusion protein.

12. The fusion protein of claim 11, wherein the fusion protein is lipidated.

13. The fusion protein of claim 11, wherein the lipidating sequence includes the sequence of SEQ ID NO: 12.

14. An isolated nucleic acid comprising a sequence encoding the fusion protein of claim 11 or a complement thereof.

15. The nucleic acid of claim 14, wherein the nucleic acid contains the sequence of SEQ ID NO: 15.

16. An expression vector comprising the nucleic acid of claim 14.

17. An isolated host cell comprising the nucleic acid of claim 14.

18. The host cell of claim 17, wherein the host cell is an *E. coli* cell.

19. An immunogenic composition comprising a fusion protein of claim 11.

20. The immunogenic composition of claim 18, wherein the composition further comprises a pharmaceutically acceptable adjuvant.

21. A method of inducing an immune response in a subject against a tumor-associated antigen, comprising administering to a subject in need thereof an effective amount of a composition containing a fusion protein of claim 11.

22. A method of producing a fusion protein, comprising
   culturing a host cell comprising the nucleic acid of claim 14 in a medium under conditions permitting expression of a fusion protein encoded by the nucleic acid, and
   purifying the fusion protein from the cultured cell or the medium.

* * * * *